United States Patent [19]

Bollum et al.

[11] Patent Number: 5,037,756
[45] Date of Patent: Aug. 6, 1991

[54] RECOMBINANT DNA MOLECULES FOR PRODUCING TERMINAL TRANSFERASE-LIKE POLYPEPTIDES

[75] Inventors: Frederick J. Bollum, Potomac, Md.; Lucy M. S. Chang, Vienna, Va.; Ronald C. Peterson, Gaithersburg, Md.

[73] Assignee: The United States of America as represented by the Secretary of the Army, Washington, D.C.

[21] Appl. No.: 854,468

[22] Filed: Apr. 21, 1986

[51] Int. Cl.$^5$ .................. C12N 15/52; C12N 15/63; C12N 1/21

[52] U.S. Cl. ................. 435/252.3; 435/69.1; 435/71.1; 435/170; 435/172.1; 435/172.3; 435/193; 435/235.1; 435/240.2; 435/320.1; 536/27; 935/6; 935/9; 935/14; 935/22; 935/59; 935/60; 935/61; 935/66; 935/72; 935/73

[58] Field of Search .............. 435/69.1, 70, 172.1, 435/172.3, 240.2, 193, 235, 320, 253; 530/350, 837; 536/27; 935/4, 9, 110, 11, 14

[56] References Cited

U.S. PATENT DOCUMENTS 4,667,017 5/1987 Ishida ............................. 530/402

OTHER PUBLICATIONS

Landau et al., Proc. Natl. Acad. Sci., vol. 81 (1984) pp. 5836–5840.
Peterson et al., Proc Natl. Acad. Sci., vol. 81 (1984) 4363–4367.
Peterson et al., Journal of Biol. Chem. Sep. 1985, vol. 260, 10495–10502
Pouwels et al., Cloning Vectors, 1985, p. IA IV20.

Primary Examiner—Robin L. Teskin
Assistant Examiner—Richard C. Peet
Attorney, Agent, or Firm—Werten F. W. Bellamy; Anthony T. Lane

[57] ABSTRACT

This invention concerns an isolated DNA sequence encoding human terminal deoxynucleotidyl transferase as well as vectors and transformed hosts carrying said DNA sequence.

10 Claims, 3 Drawing Sheets

Structure of the pUCI9(BamHI-EcoRI)/pT223 Molecule

Human Terminal Deoxynucleotidyl Transferase cDNA

Composition:  595 A,  405 C,  542 G,  526 T          Length: 2068

```
            10         20         30         40         50         60
   1 TCATTGGGTG ATTGATTTCT ATGCTCCTTG GTGTGGACCT TGCCAGAATT TTGCTCCAGA
  61 ATTTGAGCTC TTGGCTAGGA TGATTAAAGG AAAAGTGAAA GCTGGAAAAG TAGACTGTCA
 121 GGCTTATGCT CAGACATGCC AGAAAGCTGG GATCAGGGCC TATCCAACTG TTAAGTTTTA
 181 TTTCTACGAA AGAGCAAAGA GAAATTTTCA AGAAGAGGGG GGGGGGGGGG CCCCCCCCAA
 241 AAACCCTTCG TGTAGGAGGG TGGCAGTCTC CCTCCCTTCT GGAGACACCA CCAGATGGGC

301 CAGCCAGAGG CAGCAGCAGC CTCTTCCCAT GGATCCACCA CGAGCGTCCC ACTTGAGCCC
 361 TCGGAAGAAG AGACCCCGGC AGACGGGTGC CTTGATGGCC TCCTCTCCTC AAGACATCAA
 421 ATTTCAAGAT TTGGTCGTCT TCATTTTGGA GAAGAAAATG GGAACCACCC GCAGAGCGTT
 481 CCTCATGGAG CTGGCCCGCA GGAAAGGGTT CAGGGTTGAA AATGAGCTCA GTGATTCTGT
 541 CACCCACATT GTAGCAGAGA ACAACTCGGG TTCGGATGTT CTGGAGTGGC TTCAAGCACA

601 GAAAGTACAA GTCAGCTCAC AACCAGAGCT CCTCGATGTC TCCTGGCTGA TCGAATGCAT
 661 AGGAGCAGGG AAACCGGTGG AAATGACAGG AAAACACCAG CTTGTTGTGA AAGAGACTA
 721 TTCAGATAGC ACCAACCCAG GCCCCCCGAA GACTCCACCA ATTGCTGTAC AAAAGATCTC
 781 CCAGTATGCG TGTCAGAGAA GAACCACTTT AAACAACTGT AACCAGATAT TCACGGATGC
 841 CTTTGATATA CTGGCTGAAA ACTGTGAGTT TAGAGAAAAT GAAGACTCCT GTGTGACATT

901 TATGAGAGCA GCTTCTGTAT TGAAATCTCT GCCATTCACA ATCATCAGTA TGAAGGACAC
 961 AGAAGGAATT CCCTGCCTGG GGTCCAAGGT GAAGGGTATC ATAGAGGAGA TTATTGAAGA
1021 TGGAGAAAGT TCTGAAGTTA AAGCTGTGTT AAATGATGAA CGATATCAAT CCTTCAAACT
1081 CTTTACTTCT GTATTTGGAG TGGGGCTGAA GACTTCTGAG AAGTGGTTCA GGATGGGTTT
1141 CAGAACTCTG AGTAAAGTAA GGTCGGACAA AAGCCTGAAA TTTACACGAA TGCAGAAAGC

1201 AGGATTTCTG TATTATGAAG ACCTTGTCAG CTGTGTGACC AGGGCAGAAG CAGAGGCCGT
1261 CAGTGTGCTG GTTAAAGAGG CTGTCTGGGC ATTTCTTCCG GATGCTTTCG TCACCATGAC
1321 AGGAGGGTTC CGGAGGGGTA AGAAGATGGG GCATGATGTA GATTTTTTAA TTACCAGCCC
1381 AGGATCAACA GAGGATGAAG AGCAACTTTT ACAGAAAGTG ATGAACTTAT GGGAAAAGAA
1441 GGGATTACTT TTATATTATG ACCTTGTGGA GTCAACATTT GAAAAGCTCA GGTTGCCTAG

1501 CAGGAAGGTT GATGCTTTGG ATCATTTTCA AAAGTGCTTT CTGATTTTCA AATTGCCTCG
1561 TCAAAGAGTG GACAGTGACC AGTCCAGCTG GCAGGAAGGA AAGACCTGGA AGGCCATCCG
1621 TGTGGATTTA GTTCTGTGCC CCTACGAGCG TCGTGCCTTT GCCCTGTTGG GATGGACTGG
1681 CTCCCGGTTT GAGAGAGACC TCCGGCGCTA TGCCACACAT GAGCGGAAGA TGATTCTGGA
1741 TAACCATGCT TTATATGACA AGACCAAGAG GATATTCCTC AAAGCAGAAA GTGAAGAAGA

1801 AATTTTTGCG CATCTGGGAT TGGATTATAT TGAACCGTGG GAAAGAAATG CCTAGGAAAG
1861 TGTTGTCAAC ATTTTTTCCT ATTCTTTTCA AGTTAAATAA ATTATGCTTC ATATTAGTAA
1921 AAGATGCCAT AGGAGAGTTT GGGGTTATTT AGGTCTTATT GAATGCAGA TTGCTACTAG
1981 AAATAAATAA CTTTGGAAAC ATGGGAAGGT GCCACTGGTA ATGGGTAAGG TTCTAATAGG
2041 CCATGTTTAT GACTGTTGCA TAGAATTC
```

FIG. 2

Complete Amino Acid Sequence of Human Terminal

Deoxynucleotidyl Transferase (Translated from cDNA)

```
          5         10        15        20        25        30
  1   M D P P R A S H L S P R K K R P R Q T G A L M A S S P Q D I
 31   K F Q D L V V F I L E K K M G T T R R A F L M E L A R R K G
 61   F R V E N E L S D S V T H I V A E N N S G S D V L E W L Q A
 91   Q K V Q V S S Q P E L L D V S W L I E C I G A G K P V E M T
121   G K H Q L V V R R D Y S D S T N P G P P K T P P I A V Q K I
151   S Q Y A C Q R R T T L N N C N Q I F T D A F D I L A E N C E
181   F R E N E D S C V T F M R A A S V L K S L P F T I I S M K D
211   T E G I P C L G S K V K G I I E E I I E D G E S S E V K A V
241   L N D E R Y Q S F K L F T S V F G V G L K T S E K W F R M G
271   F R T L S K V R S D K S L K F T R M Q K A G F L Y Y E D L V
301   S C V T R A E A E A V S V L V K E A V W A F L P D A F V T M
331   T G G F R R G K K M G H D V D F L I T S P G S T E D E E Q L
361   L Q K V M N L W E K K G L L L Y Y D L V E S T F E K L R L P
391   S R K V D A L D H F Q K C F L I F K L P R Q R V D S D Q S S
421   W Q E G K T W K A I R V D L V L C P Y E R R A F A L L G W T
451   G S R F E R D L R R Y A T H E R K M I L D N H A L Y D K T K
481   R I F L K A E S E E E I F A H L G L D Y I E P W E R N A
```

Composition

| | | | | |
|---|---|---|---|---|
| 31 Ala A | 20 Gln Q | 50 Leu L | 38 Ser S |
| 37 Arg R | 41 Glu E | 39 Lys K | 27 Thr T |
| 13 Asn N | 26 Gly G | 13 Met M | 9 Trp W |
| 30 Asp D | 8 His H | 28 Phe F | 11 Tyr Y |
| 9 Cys C | 23 Ile I | 20 Pro P | 35 Val V |

Mol. Wt. (unmodified chain) = 58,308

Number of residues = 508

FIG. 3

RECOMBINANT DNA MOLECULES FOR PRODUCING TERMINAL TRANSFERASE-LIKE POLYPEPTIDES

BACKGROUND OF THE INVENTION

1. Field of the Invention

This invention relates to recombinant DNA molecules and their use in producing terminal deoxynucleotidyl transferase-like polypeptides. More particularly, the invention relates to recombinant DNA molecules expressed in appropriate host organisms. The recombinant DNA molecules disclosed herein are characterized by containing DNA sequences that code for polypeptides having an immunological or biological activity of human terminal transferase. As will be appreciated from the disclosure to follow, the recombinant DNA molecules of this invention may be used in the production of polypeptides useful for production of active enzymes for modification of DNA molecules and in production of antigen to generate diagnostic and analytical reagents.

2. Prior Disclosure

All publications or patents mentioned in this specification are herein incorporated by reference.

In this application the words "terminal deoxynucleotidyl transferase" refers to a protein originally isolated from calf thymus gland and having the unique property of being able to catalyze the polymerization of deoxynucleoside triphosphates in the presence of a suitable initiator molecule, also being made of DNA monomers. In the chemical literature the molecules produced might be called "block copolymers" or "graft copolymers". The full name referred to above is also abbreviated to "terminal transferase" or "TdT" for convenience, and may also be referred to by its accepted classification by the International Committee on Enzyme Nomenclature as EC 2.7.7.31. The reaction carried out by this enzyme can be summarized in the chemical formulation:

n dNTP+initiator→initiator-(dNMP)n+n pyrophosphate where dNTP stands for deoxynucleoside triphosphate, initiator is a short piece of DNA molecule containing at least 3 monomer residues and a free 3'—OH, and pyrophosphate is a molecule liberated from the activated form of the nucleotide monomer (the dNTP). The N is dNTP refers generally to a heterocyclic base, usually adenine, guanine, cytosine, or thymine, but other derivatives of these bases may also be in this reaction.

The TdT enzyme activity formulated above was first described in 1960 (F. J. Bollum, 1960, *J. Biol. Chem.*, 235, pg 18) as a side reaction present in partially purified DNA polymerase preparations from calf thymus glands. The activity was shown to polymerize deoxynucleotides onto a preformed initiator without template direction. At that time this terminal addition activity was presumed to be related to DNA polymerase as some form of active subunit (see F. J. Bollum, 1974, *The Enzymes*, Academic Press, New York pp 145–184). TdT was subsequently demonstrated to be a unique entity by tissue localization (L. M. S. Chang, 1974, *Biochem. Biophys. Res. Comm.*, 44, 124–131; M. S. Coleman, J. J. Hutton and F. J. Bollum, 1974, Blood, 44:19–32). Successful purification of TdT from calf thymus glands (L. M. S. Chang and F. J. Bollum, 1971, *J. Biol. Chem.*, 246, 909–916) and production of immuno-affinity purified rabbit antibodies to calf thyms TdT (F. J. Bollum, 1975, *Proc. Nat'l. Acad. Sci., USA*, 72, 4119–4122) allowed further studies on tissue localization and the demonstration that TdT protein is highly conserved in the animal world (F. J. Bollum and L. M. S. Chang, 1981, *J. Biol. Chem.*, 256, 8767–8770). It is clear today that TdT is indeed a most rare and unusual DNA polymerase found only in pre-lymphocytes in early stages of lymphoid differentiation. The restriction of tissue localization to specific thymus and bone marrow cells and the detection of the expanded TdT-positive population occurring in accute leukemias resulted in practical rewards that were totally unpredicted. Today, immunochemical (F. J. Bollum, 1979, Blood, 54, 1203–1215) and enzymatic determinations of TdT provide the basis of diagnostic classification of human lymphoid leukemia in the pre-B and pre-T lineages (L. M. S. Chang and F. J. Bollum, *Advances in Cancer Research*, 1986) and differential diagnosis of myeloid leukemias. The cell biology of TdT and uses of TdT as in leukemia diagnosis has been discussed in several reviews (vide supra).

Although the publication by Landau et al. (N. R. Landau, T. P. St. John, I. L. Weissman, S. C. Wolf, A. E. Silverstone and D. Baltimore, 1984, *Proc. Nat'l. Acad. Sci., USA*, 81, 5836–5840), alleges to have isolated a mouse TdT cDNA plasmid, it contains no sequence information and therefore does not instruct and it therefore would not enable one of ordinary skill in the art to practice our invention. Other results such as those disclosed by R. C. Peterson, L. C. Cheung, R. J. Mattaliano, L. M. S. Chang and F. J. Bollum, 1984, *Proc. Nat'l. Acad. Sci., USA*, 81, 4363–4367, are limited to the finding that only 30% of the cDNA sequence claimed in this application and could not by itself produce the cDNA sequence as claimed.

Employment of TdT to modify DNA molecules by adding homopolymer tails to isolated DNA molecules (D. A. Jackson, R. H. Symons and P. Berg, 1972, *Proc. Nat'l. Acad. Sci., USA*, 69, 2904–2909); P. E. Lobban and A. D. Kaiser, 1973, *J. Mol. Biol.*, 78:453–469) provided the first method for producing test tube recombinant DNAs and remains as an important tool in recombinant DNA technology. There are now many practical uses for this enzyme (F. J. Bollum, 1981, TIBS, 6, 41–43). The invention described provides a new way for producing this rare material in rapid ways and with new versatility.

SUMMARY OF THE INVENTION

The present invention solves the problem of producing TdT by first isolating the DNA sequence that codes for TdT in a recombinant plasmid. The DNA sequence containing this code is then determined. Once the complete sequence is known the whole sequence or specific parts of it can be removed from the original plasmid and inserted in tandem with a variety of non-homologous control elements that are available from other cells and viruses and these various parts joined together into an infective replicating DNA vector. The combination of these elements in the appropriate linear arrangement in the infective vector then allows the expression of the TdT sequence originally present in human cells to be expressed in a variety of other cells, including bacterial and animal cell types.

By virtue of this invention it is possible to design bacterial systems containing the recombinant molecules constructed that will express TdT enzyme activity. This protein can be isolated from the bacterial extracts and purified. Further engineering of the TdT DNA sequence allows the production of polypeptide derivatives of TdT that may have enzyme activity or may be used as antigens to produce antibodies that will detect only selected regions of the TdT molecule Modification of the TdT DNA sequence in the recombinant DNA molecules described also may permit modification of enzyme activity that might extend the uses of TdT, for example, to accept new substrate derivatives that might be used for stepwise synthesis of DNA molecules. This would provide a new enzymatic approach for manufacturing DNA sequences in a most convenient and efficient way.

Our invention is unique in that it contains the first description of the complete structure of the DNA coding sequence for TdT. Once having this sequence it is possible to make modifications by adding certain other control elements such as other promoters and ribosome binding sites in the appropriate orientation to force the expression of the TdT protein. These features are demonstrated in this application.

BRIEF DESCRIPTION OF THE DRAWINGS

A more complete appreciation of the invention and many of the attendant advantages thereof will be readily obtained by reference to the following detailed description when considered in conjunction with the accompanying drawings, wherein:

FIG. 2 shows the composition and nucleotide sequence of the human terminal deoxynucleotidyl transferase cDNA.

FIG. 3 shows the composition and complete amino acid sequence of human terminal deoxynucleotidyl transferase (translated from cDNA).

DETAILED DESCRIPTION OF THE INVENTION

Figure 1:
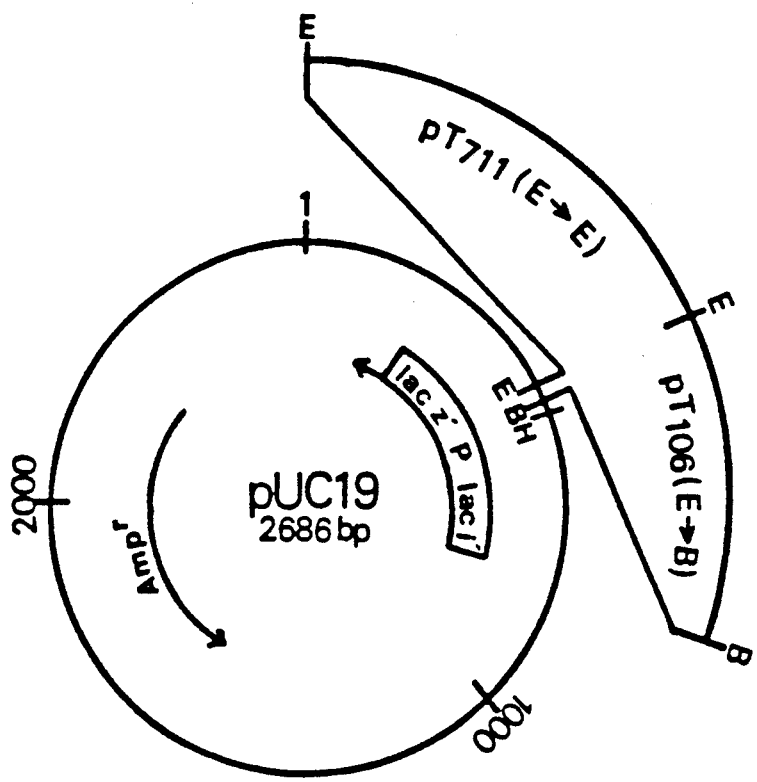
FIG. 1 illustrates the structure of the pUC19(BamHI/EcoRl)/pT223 Molecule.

Practical utility has been established for a recombinant DNA molecule consisting of segments of DNA from different genomes joined end-to-end in a circular configuration outside living cells, and having the capacity to infect certain host cells, to be maintained therein, and the progeny thereof, comprising:
  a. the DNA vector pUC19,
  b. a segment of DNA containing the lac promoter and with the coding sequence in phase with the lac Z' insert, and
  c. a DNA sequence selected from the group consisting essentially of,
    (1) the pT223/BamHI/EcoRl insert containing the complete coding sequence of the human terminal deoxynucleotidyl ransferase (minus N-terminal methionine),
    (2) DNA sequences that code for the expression of the DNA sequence described in c. (1) herein, with or without N-terminal methionine,
    (3) deletion DNA sequences derived from the TdT-DNA sequences producing polypeptides related to the conserved sequence of terminal deoxynucleotidyl transferase,
    (4) DNA sequences that hybridize to the human terminal deoxynucleotidyl transferase segment of the DNA sequences referred to in subparagraphs c. (1), (2) and (3) herein, and
    (5) any system expressing the DNA sequence hybridizing to the coding sequence for human terminal deoxynucleotidyl transferase.

The recombinant DNA molecule of this invention comprises a cloning vehicle having at least one restriction endonuclease recognition site, said DNA sequence being inserted at one of said recognition sites or between two such sites, wherein the expression control sequence is also inserted into the cloning vehicle. The expression control sequence is selected from the group consisting of a lac system, trp system, major operator and promoter regions of phage lambda, the control region of fd coat protein, and other sequences which control the expression of genes of prokaryotic or eukaryotic cells and their viruses. The unicellular host is transformed in accordance with this invention with at least one recombinant DNA molecule, said molecule, consisting of segments of DNA from different genomes as described hereinabove. Within the transformed host, the DNA sequence is operatively linked to an expression control sequence. The transformed hosts are selected from the group consisting of E. coli DH1 (pUC9 (EcoRl)/pT711) (ATCC No. 67094), E. coli HB101 (pUC8 (EcoRl)/pT106) (ATCC No. 67093), and E. coli HB101 (pUC19 (BamHl-EcoRl)/pT223) (ATCC No. 67095).

We have discovered the lambda-gtll-pT17, which is the original expression vector, pUC9-pT711, and pUC8-pT106 sequences which are essential for the performance of our genetic engineering process.

The human terminal deoxynucleotidyl transferase cDNA discovered by us has the composition and sequence as shown in FIG. 2 wherein the pT106 sequence is in nucleotides 1-966 and the pT711 sequence is in nucleotides 967-2068. Additionally, we have discovered that the terminal deoxynucleotidyl transferase protein, translated from nucleotides 329-1852 of the cDNA sequence in FIG. 2, has the amino acid composition and sequence as shown in FIG. 3. The cDNA sequence revealed in FIG. 2 and in the TdT protein sequence revealed in FIG. 3 are the essence of our discovery since they instruct and permit further synthesis and manipulation as demonstrated in Examples 1, 2, 3 and 4 of this application using methods well known in the DNA, RNA, and protein arts.

Included within the scope of the present invention are TdT sequences hybridizing to our human TdT cDNA sequence illustrated in FIG. 2 since it is known that the sequence of TdT from various living species is highly conserved (see Example 1), and, therefore, can be isolated using the information that we have discovered and disclosed in this application. This is substantiated by the disclosure in Example 1. Also within the scope of the present invention are (1) the expression of TdT cDNA as demonstrated in Example 3 and 4, and the peptides, known in the protein art, that can be modified or derivatized; and (2) the expression of polypeptides with enzyme activity produced by deletion of cDNA that codes for amino-terminal sequences, as well as, immuno-reactivity as illustrated in Example 4.

Since the production level of a protein is governed by the number of gene copies and the efficiency with which these copies are transcribed and translated (expressed) there are obvious variations that can be made on our invention. Expression is also dependent upon nucleotide sequences upstream of the protein coding region that control RNA polymerase binding and regulate the level of transcription (promoters), and other sequences that control the efficiency of the interaction of the mRNA with ribosomes (ribosome binding sites). Thus removal of the TdT cDNA coding sequence and insertion behind other promoters and ribosome binding sites to provide more efficient expression or different locale of expression or insertion into plasmids expressing greater numbers of gene copies per cell are processes well known in the genetic engineering art and are contemplated within the scope of the present invention. The unicellar hosts which are transformed in accordance with this invention can employ cloning vehicles comprising a microbial or yeast plasmid, or a virus and mixtures thereof. The virus can be a bacteriophage, animal virus, plant virus, or insect virus.

The invention now being described will be better understood by reference to certain specific examples which are included herein for purpose of illustration only and are not intended to be limiting for the purpose of the invention or any embodiment thereof, unless specified.

METHODS FOR DISCOVERING MOLECULES WITH TdT DNA SEQUENCE

Preparation of Poly (A) RNA Containing Human TdT mRNA

A poly (A) RNA mixture containing human TdT mRNA was prepared using a procedure modified from Adrian and Hutton (G. S. Adrian and J. J. Hutton, 1983, *J. Clin. Invest.*, 71, 1649–1660). Human lymphoblastoid KM-3 cells were harvested and $5 \times 10^9$ cells were suspended in 100 ml of ice cold solution containing 3 M LiCl, 10 mM sodium acetate (NaAc) at pH 5.0, 6 M urea, 0.1% sodium dodecyl sulfate (SDS), 2 mg/ml heparin and 6 mM vanadyl ribonucleoside complex (BRL) in a 250 ml sterile beaker. The suspension was homogenized with 3 twenty second high speed bursts in a Polytron Homogenizer. The homogenate was transferred into five 40 ml polycarbonate tubes in 20 ml aliquots and RNA was allowed to precipitate at $-20°$ C. for overnight. Precipitates in the tubes were collected by centrifugation for 25 minutes in the SS-34 rotor in a Sorvall 5B Centrifuge at 17,000 revolutions per minute (rpm) at 4° C..

The supernatant solutions were removed by decantation, and the pellet in each centrifuge tube was dissolved in 8 ml sterile water by heating at 60° C. for 5 minutes. The redissolved crude RNA solution was transferred into sterile 30 ml Corex tubes. To remove contaminating protein the RNA was extracted with 8 ml of redistilled phenol saturated with 0.3 M NaAC at pH 5.0 and 0.3% SDS was added. After mixing, 8 ml of chloroform was added to each tube and the tubes were swirled on ice for 5 minutes. Phase separation was carried by centrifugation for 10 minutes at 12,000 rpm in the SS-34 rotor in a Sorvall centrifuge at 4° C. After centrifugation, the top layer (aqueous) in each tube was transferred with sterile pasteur pipettes into new sterile Corex tubes, and the phenol:chloroform extraction was repeated as before. After the second phenol:chloroform treatment, the aqueous layer from each tube (7.5 ml) was again transferred into a clean sterile Corex tube, 0.7 ml of 3 M NaAc at pH 6.0 was added. RNA was precipitated from these solutions by addition of 2.5 volumes of ice cold ethanol to each tube and allowing to stand overnight at $-20°$ C.

The RNA precipitate that formed overnight was collected by centrifugation for 10 minutes at 10,000 rpm in a SS-34 rotor in the Sorvall Centrifuge at 4° C. The ethanol supernatant was removed by decantation. The RNA pellets have a greenish color due to the presence of vanadyl ribonucleoside complex. This color is extracted by resuspension of the pellets twice in 3 M NaAc at pH 6.0 (8 ml per tube) and collection of precipitates by centrifugation for 10 minutes at 10,000 rpm in a SS-34 rotor in the Sorvall Centrifuge at 4° C. The pellet was then resuspended in 8 ml of 70% ethanol to remove NaAc and collected by centrifugation. Each pellet was then dissolved in about 0.5 ml of sterile water and combined, yielding about 2.7 ml in one Corex tube. RNA recovered totalled 14 mg, as measured by absorbance at 260 nm. Total RNA was precipitated by addition of 0.3 ml of 3 M NaAc at pH 6.0 and 7.5 ml of ice cold ethanol. After standing overnight at $-20°$ C., precipitated RNA was collected by centrifugation and redissolved in 14 ml of sterile water to produce a 1 mg/ml solution of total RNA.

Isolation of the poly (A) containing RNA (the mRNA molecules) from the total RNA mixture was accomplished by two cycles of adsorption and elution from a $1 \times 3$ cm oligo dT cellulose (type 7, P-L Biochemicals, Inc.) column. Prior to loading the poly (A) mRNA onto the oligo dT cellulose column, the RNA in solution was first denatured by warming to 75° C. for 5 minutes, and rapidly cooled in an ice bath. 5 M NaCl, 10 X TE buffer (10 mM Tris:HCl at pH 7.4 and 1 mM EDTA) was added to the RNA solution to final concentration of 0.5 M NaCl in 1X TE buffer. This RNA solution was loaded onto the oligo dT cellulose column previously equilibrated with 0.5 M NaCl in TE. After loading, the column was washed with 50 ml 0.5 M NaCl in TE, and poly (A) containing mRNA mixture was eluted from the column with TE buffer. Absorbance at 260 nm was measured in each fraction collected from the column during elution and those fractions having $A_{260}$ greater than 0.05 were pooled to yield 8 ml of solution containing 650 micrograms of RNA. The NaCl concentration of this column pool was adjusted to 0.5 M and the pool was re-loaded onto another identical column. The second elution gave a pool of 6.5 ml with 520 micrograms of poly (A) mRNA mixture.

The poly (A) mRNA mixture purified on oligo dT cellulose column was concentrated by precipitation with ethanol in the presence of NaAc as described above and redissolved in sterile water as a 1 mg per ml solution and stored in a liquid $N_2$ freezer.

Total mRNA was assayed for the presence of TdT-mRNA by in vitro translation of the total mRNA using a rabbit reticulocyte system for protein synthesis and analysis by immunoprecipitation of the translated products. In vitro translation reactions were carried out essentially as described by Pelham and Jackson (H. R. B. Pelham, and R. J. Jackson, 1976, *Eur. J. Biochem.*, 247, 247–256). Translation reactions (60 microliters) contained 10 micrograms poly (A) mRNA mixture, 20 microliters rabbit reticulocyte lysate (BRL), 25 mM Hepes buffer at pH 7.5, 50 mM potassium acetate at pH 7.5, 15 mM creatine phosphate, 30 mM KCl, 1 mM Mg acetate, 50 micromolar of each of the 19 amino acids, 0.25 mM phenylsulfonylfluoride, and 3 micromolar $^{35}$S-methionine (100 microcuries, Amersham). After incubation at 30° C. for 90 minutes, 30 microliters of 0.6 mg/ml puromycin, 20 mM methionine, 3 mM phenylsulfonylfluoride in 3% dimethylsulfoxide was added and incubation was allowed to continue for 5 minutes at 30° C. The reaction mixtures were then clarified by centrifugation for 30 minutes at 28 p.s.i. in a Beckman Airfuge at room temperature. Each supernatant was transferred to an Eppendorf centrifuge tube, and diluted with 120 microliters of 0.2 M NaCl, 0.1 M Tris:HCl at pH 8.0, 0.5% NP-40 and 40 mM methionine. Two (2) micrograms of immuno-affinity purified rabbit antibody to TdT was added to precipitate the specific TdT product, if any. The mixture was incubated at room temperature for 2 hours. The immune complexes formed were absorbed onto formaldehyde-treated *Staphylococcus aureus* cells (S. Kessler, 1975, *J. Immunol.*, 115, 1617–1624). Proteins in the immune complexes on *S. aureus* cells were dissociated in SDS buffer, analyzed by electrophoresis on a 12.5% polyacrylamide gel in the presence of SDS (U. K. Laemmli and M. Favre, 1973, *J. Mol. Biol.*, 80, 575–599) and detected on the gel by fluorography.

The autoradiogram of the gel containing the in vitro translated and immunoprecipitated products of the poly (A) mRNA from KM-3 cells showed a radioactive peptide at 58 kDa, the same molecular weight as TdT found naturally in human lymphoblastoid cells (F. J. Bollum and M. Brown, 1979, *Nature* 278, 191). This 58 kDa band was not formed from the in vitro translation and immunoprecipitation products of poly (A) mRNA from TdT-negative human lymphoblastoid cells, and was not present when the poly (A)-negative RNA fraction from KM-3 cells was used in the translation reaction. Quantitation of the level of translated product that can be precipitated with the TdT antibody showed that less than 0.001% of protein synthesized in the in vitro translation to be TdT, although TdT constitutes about 0.1% of total protein in human KM-3 cells. Nevertheless, the in vitro translation and immunoprecipitation with antibody to TdT showed that mRNA for TdT is present in the poly (A) mRNA fraction of KM-3 cells.

Construction of KM-3 Cell cDNA Libraries in Lambda gt 11 Phage

Since TdT mRNA represents a minor message in the cell, traditional purification of this specific mRNA is not technically feasible Cloning of the cDNA in an expression vector and expression of the recombinant protein in suitable host cells provides a method for screening for the presence of TdT cDNA sequence in recombinant phages or plasmids by immunological reactions. The lambda gt 11 vector developed by Young and Davis (R. Young and R. W. Davis, 1983, *Proc. Nat'l. Acad. Sci., USA,* 80, 1194–1198) was chosen as appropriate cloning vector since it has a 17 single EcoRl restriction site located at the 3'-end of the coding sequence for *E. coli* beta-galactosidase. When a DNA sequence is ligated into the EcoRl site, translation of the carboxyl-terminal region of beta-galactosidase amino acid sequence is interrupted and an inactive beta-glactosidase protein is produced. Recombinant phage can be selected as colorless plaques when plated with appropriate bacterial host cells on X-Gal plates. Recombinants having the inserted DNA sequence in phase with the beta-galactosidase sequence will express a fused protein containing the bulk of beta-galactosidase amino acid sequence followed by the amino acid sequence of TdT. This fused protein can be identified by reaction with antibodies specific for the immunological determinants expressed in the TdT portion of the cloned and expressed sequences.

Two KM-3 cell cDNA libraries were constructed in order to isolate the full coding sequence of human TdT. In the first KM-3 cell cDNA library in lambda gt 11 (No. 62) internal EcoRl sites in the double-stranded KM-3 cell cDNA were not protected by methylation. Screening of this library for TdT sequence expression was carried out by reaction of the fused protein with affinity purified rabbit antibodies to calf thymus TdT. Several recombinant clones were isolated from library No. 62. The second KM-3 cell cDNA library in lambda gt 11 was constructed with fractionated KM-3 cell double-stranded cDNA fully methylated with EcoRl methylase (No. 201) and was screened with a nick-translated TdT cDNA fragment isolated from library No. 62. A recombinant containing full length coding sequence for TdT was isolated from library No. 201.

To produce the lambda gt 11 libraries a double-stranded cDNA copy of the mRNA must be prepared. Single-stranded KM-3 cDNA was synthesized in a reaction (0.75 ml) containing 75 micrograms KM-3 poly (A) RNA, 50 mM Tris:HCl buffer at pH 8.3, 50 mM KCl, 10 mM $MgCl_2$, 30 mM 2-mercaptoethanol, 25 micrograms/ml oligo $(dT)_{12-18}$ (P-L BioohemIoaIs), 0.5 mM each dATP, dTTP, dGTP and 0.5 mM $^3$H-dCTP at 9 counts/minute/pmole, 40 micrograms/ml actinomycin D and 750 units AMV reverse transcriptase. Incubation was for 75 minutes at 42° C., and the reaction was terminated by addition of EDTA to 20 mM. Analysis of acid-insoluble radioactive product determined by liquid scintillation counting showed 19.5 micrograms of DNA was synthesized in this reaction. The mRNA template was hydrolyzed by addition of NaOH to 150 mM and incubation at 65° C. for 1 hour. After neutralization of the reaction mixture with HCl, Tris:HCl buffer at pH 8.0 was added to 0.2 M. Protein in the reaction mixture was removed by phenol:chloroform extraction, and the products of the synthesis were isolated by gel filtration on a 1×50 cm Sephadex G-50 (Pharmacia) column in TE buffer. Sephadex G-50 column fractions containing radioactive polynucleotides were pooled to give 2.9 ml containing 15.8 micrograms cDNA that was concentrated by precipitation with ethanol in the presence of NaAc as described above and redissolved in 0.16 ml of sterile water.

The single-stranded KM-3 cDNA was tailed with a stretch of dC in a terminal transferase catalyzed reaction (0.28 ml) containing 14 micrograms single-stranded cDNA, 1 mM dithiothreitol, 0.1 M potassium cacodylate buffer at pH 7.2, 0.3 mM $^3$H-dCTP at 90 counts/minute/pmole, 1 mM $CoCl_2$, 100 micrograms/ml bovine serum albumin (BSA) and 120 units of calf thymus TdT. Incubation was for 20 minutes at 37° C., and the reaction was terminated by addition of EDTA of 10 mM. Products of the tailing reaction were isolated by removal of protein with phenol:chloroform extraction, precipitation with ethanol in the presence of NaAc, and redissolving in 0.11 ml of sterile water. The incorporation of $^3$H-dCMP into acid-insoluble products showed an average of 30 dC residues added per RNA molecule and a recovery of 11 micrograms of dC-tailed single-stranded KM-3 cDNA.

Second strand cDNA synthesis was carried out in a reaction mixture (1.1 ml) containing 11 micrograms dC-tailed cDNA, 25 micrograms/ml oligo $(dG)_{12-18}$ (P-L Biochemicals), 1 mM dithiothreitol, 50 mM Tris:HCl buffer at pH 8.3, 50 mM KCl, 100 micrograms/ml BSA, 10 mM $MgCl_2$, 0.5 mM each dATP, dGTP, dTTP and $^3$H-dCTP at 90 counts/minute/pmole and 475 units of AMV reverse transcriptase. The dC-tailed cDNA and oligo dG were pre-mixed and heated at 65° C. for 10 minutes followed by slow cooling to allow efficient annealing prior to addition to the reaction. Incubation was for 60 minutes at 37° C. and the reaction was terminated by addition of EDTA and SDS to 20 mM and 0.5%, respectively. Products of the reaction were obtained after deproteinization by phenol:chloroform extraction, precipitation with ethanol in the presence of NaAc, and redissolving in 0.15 ml TE buffer. Analysis of the polymerization of radioactive dCTP showed the replication was near 100% and the total double-stranded cDNA recovered was 22 micrograms.

The double-stranded cDNA from KM-3 was treated with the large fragment of E coli DNA polymerase I in order to generate blunt ends suitable for ligation with EcoRl linkers. This was accomplished in a reaction mixture (0.3 ml) containing 22 micrograms double-stranded cDNA, 50 mM Tris:HCl buffer pH 7.5, 7 mM MgCl$_2$, 0.4 mM each dATP, dCTP, dGTP and dTTP, 50 mM NaCl and 40 units of large fragment of E. coli DNA polymerase I (New England Biolabs), and incubation at 30° C. for 30 minutes. Double-stranded cDNA was recovered from this reaction after phenol:chloroform extraction, ethanol precipitation, and redissolved in 40 microliters of TE buffer.

Phosphorylation of the EcoRl linker was carried out in a reaction (10 microliters) containing 2 micrograms of EcoRl linker Collaborative Res.), 75 mM Tris:HCl buffer at pH 7.6, 10 mM MgCl$_2$ and 5 mM dithiothreitol, 20 microcuries of gamma-$^{32}$P-ATP (ICN) and 12 units of bacteriophage T$_4$ polynucleotide Kinase (Collaborative Res.). After incubation at 37° for 30 minutes, 10 microliters of 2 mM ATP and 12 units T$_4$ polynucleotide kinase in 75 mM Tris:HCl buffer at pH 7.6, 10 mM MgCl$_2$, 5 mM dithiothreitol were added and incubation was allow to continue for an additional 30 minutes at 37° C. The phosphorylated EcoRl linker was used in a ligation reaction with the double-stranded cDNA from KM-3 cells prepared as described above. Ligation was carried out in a reaction mixture (50 microliters) containing 20 micrograms double-stranded cDNA, 1 microgram $^{32}$P-EcoRl linkers, 50 mM Tris:HCl buffer at pH7.6, 1 mM spermidine, 10 mM MgCl$_2$, 10 mM dithiothreitol, 0.1 mg/ml BSA, 0.4 mM ATP and 2.5 units of bacteriophage T$_4$ ligase (Collaborative Res.). After incubation at 12° C. for 24 hours, the reaction mixture was heated for 10 minutes at 65° C. to inactivated the T$_4$ ligase. Polylinker sequences formed in the ligation were removed from double-stranded cDNA by addition of an equal volume of a solution containing 20 units of EcoRl nuclease in 0.2 mg/ml BSA, 0.2 M Tris:HCl buffer at pH7.2, 10 mM MgCl$_2$ and 0.1 M NaCl, and incubation for 2 hours at 37° C. EcoRl nuclease digestion was terminated by addition of EDTA to 20 mM and heating for 10 minutes at 65° C. The high molecular weight products were isolated by gel filtration on a 1×10 cm Sephadex G-50 column in TE buffer, precipitation with ethanol in the presence of NaAc, and redissolved in TE buffer to 0.5 mg/ml. About 20 micrograms of KM-3 cDNA was recovered.

The vector DNA, lambda gt 11 DNA, was cut with EcoRl nuclease and dephosphorylated with calf intestinal phosphatase to prevent self ligation during the ligation reaction with double-stranded cDNA from KM-3 cells. A typical preparation started with self ligation of 100 micrograms of lambda gt 11 DNA in a 0.2 ml reaction mixture containing 50 mM Tris:HCl buffer at pH 7.6, 10 mM MgCl$_2$, 10 mM dithiothreitol, 0.4 mM ATP, and 3.5 units of T$_4$ ligase. Reaction was carried out at 12° C. for 24 hours and terminated by heating for 10 minutes at 65° C. An equal volume of EcoRl nuclease reaction mixture containing 0.2 M Tris:HCl buffer at pH7.2, 10 mM MgCl$_2$, 0.1 M NaCl, 0.1 mg/ml BSA, and 200 units of EcoRl nuclease was added to the terminated ligation reaction. Incubation was carried out for 4 hours at 37° C. The reaction was terminated by addition of EDTA, NaAc at pH 5.0, and SDS to final concentrations of 20 mM, 0.3 M and 0.5%, respectively. After heating for 10 minutes at 65° C., products of the digestion were isolated by phenol:chloroform extraction, ethanol precipitation, the EcoRl cleaved lambda gt 11 DNA was removed by incubation of the DNA at 37° C. in a reaction mixture (0.25 ml) containing 0.05 M Tris-HCl at pH 8.0, 0.1 mM EDTA and 2 units of calf intestinal alkaline phosphatase (Boehringer Mannheim). An additional 1 unit of calf intestinal alkaline phosphatase was added after 30 minutes of incubation and the reaction was allowed to continue for an additional 30 minutes. The reaction was terminated by addition of Tris:HCl, NaCl and SDS to 50 mM, 0.1 M and 0.5%, respectively. After heating for 10 minutes at 65° C., dephosphorylated DNA product was isolated by phenol:chloroform extraction, ethanol precipitation and redissolving in TE buffer at 1 mg/ml.

To generate the rcombinant phage, the EcoRl cleaved dephosphorylated lambda gt 11 DNA (10 micrograms) was ligated to 3 micrograms of double-stranded KM-3 cDNA containing $^{32}$P-EcoRl linkers (as described above) in a reaction (30 microliters) containing 50 mM Tris:HCl at pH 7.6, 10 mM MgCl$_2$, 0.4 mM ATP, 5 mM dithiothreitol and 6 units of T4 ligase. Incubation was at 12° C. for 24 hours. Progress of the ligation was followed by analytical separation of the ligation mixture by electrophoresis on 0.6% agarose gel and autoradiography. Ligation was judged to be complete due to the disappearance of lower molecular weight cDNA and the appearance of radioactivity associated with the vector DNA.

Packaging of the KM-3 cDNA ligated into lambda gt 11 vector was carried out with the BRL Lambda In Vitro Packaging System according to the manufacturer's instructions. Packaging of 3 micrograms of the ligated cDNA generated 3.5×10$^6$ phages when plated on E. coli Y1090 cells. About 28% of the phages were found to form clear plaques when plated on LB plates containing the chromogenic indicator 5-bromo-4-chloro-3-indolyl beta-D-galactoside (X-Gal) indicating that this KM-3 cDNA library in lambda gt 11 (KM-3 cDNA library No. 62) contains about 1×10$^6$ recombinants.

In order to isolate the full length coding sequence for TdT, a second KM-3 cDNA library in lambda gt 11 was constructed (KM-3 cDNA library No. 201) in which the EcoRl sites in the double-stranded KM-3 cDNA were protected by methylation with EcoRl methylase, and the double-stranded cDNA was size fractionated to obtain longer fragments The procedures used were as described above with three major exceptions:

A. An oligo (dG) tail was added onto single-stranded cDNA using the same TdT reaction conditions described above, and the double-stranded cDNA synthesis was accomplished by using oligo (dC)$_{12-18}$ (Collaborative Res.) as initiator and the large fragment of E. coli DNA polymerase I. Twelve micrograms of single-stranded KM-3 cDNA was used in the tailing reaction by TdT and dGTP and an average of 20 dG residues are added per 3'-end. At the end of TdT reaction, the reaction mixture was heated for 10 minutes at 65° C., and template RNA was digested by addition of pancreatic RNase (Worthington Biochemicals) to 5 micrograms/ml and heating at 95° C. for 60 minutes. Oligo (dC)$_{12-18}$, 25 micrograms/ml, was also added at the same time as pancreatic RNase. After 1 hour at 95° C., the digest was slowly cooled to room temperature to allow annealing of oligo (dC) with dG-tailed single-stranded KM-3 cDNA. Second strand synthesis was carried out in a reaction mixture (0.25 ml) containing 50 mM Tris:HCl buffer at pH 7.5, 50 mM NaCl, 0.1 mM each dCTP, dATP, dTTP and dGTP, 10 mM MgSO$_4$, 11 micrograms dG-tailed KM-3 single-stranded cDNA and 25 micrograms/ml oligo (dC), and 60 units of large fragment of E. coli DNA polymerase I. Incubation was for 3 hours at 14° C., and the reaction was terminated by addition of EDTA to 20 mM and heating for 10 minutes at 68° C. Products were isolated by phenol:chloroform extraction, ethanol precipitation, and redissolving in 0.1 ml TE buffer. Replication of the cDNA was greater than 90% and the double-stranded cDNA recovered by this process was 20 micrograms.

B. Prior to ligation of double-stranded KM-3 cDNA to EcoRl linker, methylation of the EcoRl sites was carried out for 1 hour at 37° C. in a reaction (0.3 ml) containing 20 micrograms of double-stranded cDNA, 0.4 mg/ml BSA, 10 micromolar S-adenosylmethionine, 1 mM EDTA and 240 units of EcoRl methylase (BRL). The reaction was terminated by phenol:chloroform extraction. Methylated products were isolated by gel filtration on BioGel P-60 (BioRad) in TE buffer, precipitation with ethanol and redissolving in sterile water. The digestion of this cDNA with EcoRl nuclease after addition of $^{32}$P-EcoRl linkers showed no major change in size distribution suggesting that the methylation reaction was complete and all internal EcoRl sites were protected.

C. Prior to ligation with the EcoRl-cleaved phosphatase treated lambda gt 11 vector, the KM-3 cDNA with $^{32}$P-EcoRl linkers was fractionated on a 1% agarose gel. Fragments migrating with sizes between 1300 to 4000 b.p. were eluted from the agarose gel and used for ligation with the vector.

The ratio of cDNA to vector DNA used in the ligation was 2 to 15. A library (No. 201) of $1 \times 10^6$ recombinant phages was obtained from 2 micrograms of methylated and size fractionated double-stranded KM-3cDNA.

Screening of KM-3cDNA Libraries in Lambda gt 11 for Clones Expressing TdT and Clones Containing TdT cDNA Sequence Two procedures were used to screen for TdT DNA sequences present in the libraries constructed as described above. The original clones containing TdT cDNA sequence were isolated by detecting reaction of fused galactosidase-TdT protein produced by infected E. coli cells using affinity purified rabbit antibodies to calf thymus TdT. After the cloned cDNA sequence was proven to be part of the TdT cDNA sequence, the sequence isolated was used to synthesize a nick-translated DNA probe. Longer TdT cDNA sequences were then isolated by hybridization of recombinant phage plaques (DNA) with nick-translated TdT cDNA probes.

A typical immunological screening procedure was carried out as follows: Packaged lambda phages were mixed with E. coli Y1090 cells and plated on LB agar plates (150 mm×25 mm) at 15,000 plaque forming units (pfu) per plate. After incubation at 37° C. for 6 to 12 hours, a nitrocellulose filter (pretreated with 10 mM isopropylthiogalactoside (IPTG) and damp dried) was overlaid on the plate. Growth was allowed to continue for 2 hours at 37° C. The nitrocellulose filter was then removed for immmunological detection of TdT protein and the plate stored at 4° C. 12 plates and therefore 12 filters were worked-up each time. In all procedures using immunological detection, the filters were first washed for 10 minutes in a baking dish (30 cm×30 cm) with 500 ml of 50 mM Tris:HCl at pH 8.0 and 0.1 M NaCl (TBS) and then blocked by incubation for 1 hour with 300 ml of 20% fetal calf serum (FCS) in TBS. The specific immunological reaction was carried out by incubating the filters for 1 hour with 200 ml of 2 micrograms/ml immuno-affinity purified rabbit antibodies to calf thymus TdT in 20% FCS in TBS. The filters were then washed once for 10 minutes with 300 ml 0.1% NP-40 in TBS, and 3 times with 300 ml TBS for a total of 30 minutes. Antibodies bound to the filter were detected by incubation of the filters with 200 ml $^{125}$I-Protein A (New England Nuclear, 10 microcuries per filter) in TBS for 1 hour. The filters were then washed once for 10 minutes with 300 ml 0.1% NP-40 in TBS, 4 times for 10 minutes each with 300 ml TBS, dried, placed in X-ray film cassettes with intensifying screens and exposed for 2 to 4 days at −70° C. for the initial screen. Positive immunological reaction on the filters appears on the X-ray film as fuzzy black spots.

Areas on the agar plates corresponding to the dark spots on the X-ray films were located and agar plugs picked out with sterile pipettes, suspended in sterile SM (0.1 M NaCl, 10 mM MgCl$_2$, 50 mM Tris:HCl at pH 7.5 and 0.01% gelatin), and phages were dispersed from the agar by mixing for 1 hour at 37° C. The titer of phage in these suspensions was determined, and the phages were then grown up in E. coli Y1090 on LB agar plates (square, 100 mm ×15 mm) at about 1000 pfu per plate. The plates were screened for recombinants producing proteins reacting with rabbit antibodies to TdT (described above). If the presumed positive picked in the initial screen is a real recombinant phage, increased numbers of positive plaques are generally detected in the second screen and the exposure time to the X-ray film was less than 24 hours. Areas on the plate containing positive plaques were again extracted and related at less than 100 plaques per plate, re-screened by the immunological procedure described above to allow the isolation of single plaques. Five recombinants producing fused protein reacting with rabbit antibodies to TdT were isolated from KM-3 library No. 62 by screening 200,000 plaques from this library. This process is called "plaque purification".

Stocks of plaque purified recombinant phages that produce fused proteins reacting with rabbit antibodies to TdT were produced by amplification of individual plaques on LB agar plates using E. coli Y1088 as the host cell, harvesting of the plates by washing with SM, lysis of E. coli cells by shaking with chloroform, removal of cellular debris by centrifugation, concentration of the phage by polyethylene glycol (PEG) precipitation, resuspension in SM, removal of PEG by extraction with chloroform, and storage of the phage stock in SM in the presence of chloroform. Each of the phage stocks were screened again with the antibody of TdT to insure that all infectious particles were producing fused protein reacting with antibodies to TdT.

Recombinant phage DNAs were obtained from CsCl gradient purified phage by digestion for 2 hours at 37° C. with 0.1 mg/ml proteinase K (Boehringer Mannheim) in the presence of 20 mM EDTA, 0.5% SDS, 50 mM Tris:HCl at pH 7.6 and 50 mM NaCl, extraction with phenol:chloroform, precipitation with ethanol and redissolving in TE buffer. Digestion of four of the recombinant phage DNAs with EcoRl nuclease and analysis of the insert DNAs on agarose gels showed that the inserts ranged from 723 to 939 bp. These four inserts, after recloning into pBR322 as described below, are called pT16 (768 bp), pT17 (939 bp), pT18 (789 bp) and pT19 (723 bp). Restriction enzyme and preliminary sequence analyses showed that these four inserts are related in that they share the same 3'-end sequence. The pT17 insert, being the longest TdT cDNA isolated, was used to synthesize a cDNA probe in order to rescreen library No. 62 and library No. 201 for longer TdT cDNAs.

The insert in pT17 was obtained by digestion of pT17 with EcoRl nuclease, separation of the insert from pBR322 DNA by electrophoresis on a 1% agarose gel, electro-elution of the 939 bp DNA insert from the gel, and concentration of the DNA by ethanol precipitation. Nick-translated probe was typically prepared in a reaction mixture (20–50 microliters) containing 0.1–0.5 micrograms of insert DNA, 50 mM Tris:HCl at pH 7.5, 5 mM MgCl$_2$, 10 mM 2-mercaptoethanol, 50 micrograms/ml BSA, 100 microcuries of alpha-$^{32}$P-dATP, 0.3 mM each of dCTP, dGTP and dTTP, 2 nanograms/ml pancreatic DNAase I (Worthingtion Biochemicals), and 5 to 10 units of E. coli DNA polymerase I (BRL). Incubation was carried out at 16° C. for 60 minutes, and macromolecular products were isolated from the void volume of a 1×10 cm Sephadex G-50 column. The specific activity of the nick-translated probe is generally 1 to 5×10$^8$ counts/minute/microgram of DNA.

Screening of the KM-3 cDNA libraries with $^{32}$-P-nick-translated probes was typically carried out by placing untreated nitrocellulose filters on overnight cultures on LB-agar plates for 5 to 10 minutes to generate imprints of the plaques on the plates. The filters were then treated with 1.5 M NaCl in 0.5 M NaOH for 1 to 2 minutes to denatured the DNA, 1 to 2 minutes in 1.5 M NaCl in 0.5 M Tris:HCl at pH 8.0, about 5 minutes in 2x SSC (standard saline citrate), and then baked at 80° C. for 2 hours. The filters were equilibrated for 2 hours at 65° C. with hybridization buffer (4x SSC, 0.2% Ficoll, 0.2% BSA, 0.2% polyvinylpyrollidone, 0.1% SDS and 50 micrograms/ml salmon sperm DNA (Worthington Biochemicals)), and then hybridized overnight in the hybridization buffer with $^{32}$P-nick-translated DNA (10$^6$ counts/minute/filter) at 65° C. After hybridization, the filters were washed repeatedly with 0.1% SDS in SSC at 55° C. until radioactivity was absent from the wash solutions. Positive hybridization was detected by autoradiography.

Each positive recombinant phage picked was plaque purified, and the recombinant phage DNA analyzed on agarose gel following EcoRl nuclease digestion as described above. For each recombinant phage DNA separated on agarose gel after EcoRl digestion, the DNA on the gel was transferred onto nitrocellulose filter and probed with the nick-translated insert of pT17. Transfer of DNA fragments from agarose gels after electrophoresis was accomplished by first treating the gel with 0.3 M NaOH in 0.9 M NaCl for 45 minutes to denature the nucleic acid, neutralizing the gel by treatment with 0.9 M NaCl in 1 M Tris:HCl at pH 7.5, followed by transferring onto nitrocellulose sheets by capillary flow. The nitrocellulose sheet was then baked and carried through the hybridization procedure as described above.

Screening of KM-3 cDNA library No. 62 with the nick-translated insert of pT17 produced many positives, constituting about 1% of recombinants in this library. Most of the recombinants isolated by DNA hybridization have insert sizes of about 1100 bp with none having larger inserts. After recloning of this 1100 bp into pUC-9 (pT711, see below) and preliminary DNA sequence analysis, it was clear that this 1100 bp sequence is flanked by an EcoRl sequence at the 5'-end, suggesting an internal EcoRl site in the TdT cDNA.

In order to isolate the full coding sequence of TdT, KM-3 library No. 201 was constructed in which the internal EcoRl sites are protected by methylation. Using the nick-translated insert of pT711 as probe, over 30 positive recombinants were isolated from library No. 201. DNAs isolated from plaque purified positive recombinant phages were subjected to partial EcoRl digestion, and the DNAs in partial EcoRl digests were separated by electrophoresis on 1% agarose gel, transferred to nitrocellulose sheets, and probed with the nick-translated insert of pT711, in order to determine the total insert size. Only one recombinant phage had an insert size of 2100 bp, the size estimated for full length TdT cDNA. This 2100 bp insert in lambda gt 11 was recloned into pUC-8 as two fragments of 1100 bp and 1000 bp. The 1100 bp sequence is identical in sequence to the insert in pT711. The 1000 bp sequence recloned in pUC-8 is called pT106.

Subcloning Lambda cDNA Inserts into pBR322 and pUC8 and pUC9

The TdT cDNA inserts were removed from four different recombinant lambda phage clones and recloned in the plasmid pBR322. Recombinant lambda phage DNA (4 micrograms) was cleaved with 20 units of EcoRI in 100 mM Tris:HCl at pH 7.5, 50 mM NaCl, 5 mM MgCl$_2$, 1 mM dithiothreitol, 0.1 mg/ml BSA in a total volume of 20 microliters for 2 hours at 37° C. and the reaction was stopped by adding 1 microliter 0.25 M EDTA, 2 microliters 5% SDS, 2 microliters 3 M NaAc and extracted with an equal volume of phenol. The aqueous phase was extracted with an equal volume of chloroform and the DNA was precipitated with ethanol and redissolved in 10 microliters TE buffer. Two micrograms of the EcoRl cleaved recombinant lambda DNA and 0.2 micrograms EcoRl cleaved and phosphatase treated pBR322 DNA were ligated with 1 unit T4 DNA ligase in 66 mM Tris:HCl at pH 7.6, 5 mM MgCl$_2$, 5 mM thiothreitol, and 1 mM ATP in a total volume of 1 microliters at 12° C. for 16 hours and adjusted to 100 microliters by addition of TE buffer. The ligated DNA solution was used to transform E. coli DH-1 by the procedure of Hanahan (D. Hanahan, 1983, J. Mol. Biol., 166, 557–580). To prepare E. coli DH-1 for transformation, the bacteria were grown in 100 ml L-broth (1% Bacto-Tryptone, 0.5% yeast extract, 85 mM NaCl, 10 mM Tris:HCl at pH 7.5, 1 mM MgSO$_4$) at 37° C. with shaking to an optical density of 0.5 at 550 nm, chilled on ice for 15 minutes, and harvested in sterile centrifuge tubes by centrifugation (Sorvall SS-34 rotor) at 6000 rpm for 5 minutes at 4° C. The bacteria were suspended in 33 ml TFB (10 mM 4-morpholinoethane sulfonic acid adjusted to pH 6.3 with potassium hydroxide, 100 mM RbCl, 45 mM MnCl₂, 10 mM CaCl₂, 3 mM hexamine cobalt(III) chloride) incubated on ice for 15 minutes, and harvested by centrifugation as described above. The bacteria were suspended in 8 ml TFB and dimethylsulfoxide was added to 200 microliter aliquots of the bacterial suspension to give a final concentration of 3.5% dimethylsulfoxide. The bacterial suspension was incubated on ice for 15 minutes, dimethylsulfoxide was added again to give a final concentration of 7% dimethylsulfoxide and the mixture was incubated on ice for an additional 10 minutes. Two hundred microliters aliquots of the dimethylsulfoxide treated bacterial suspension were mixed with 50 microliters of each solution containing the ligated DNA samples described above and the mixtures were incubated on ice for 30 minutes and at 42° C. for 2.5 minutes. One ml L-broth was added and the tubes were incubated at 37° C. with shaking for 1 hour. Bacteria were mixed with 3.5 ml of 0.75% agar in L-broth with 50 micrograms/ml ampicillin and plated on 1% agar plates in the same media. Recombinant plasmids in the transformed bacteria were screened for inserts having the same size as the cDNA inserts in the original recombinant lambda phage clones. Representative clones were picked and called pT16, pT17, pT18, and pT19. The cDNA insert in pT17 is the longest in this group.

The cDNA insert fragment in lambda clone 711 was separated from the lambda vector DNA and recloned in the plasmid pUC9. Approximately 200 micrograms lambda clone 711 DNA was digested with 1000 units EcoRl nuclease in 100 mM Tris:HCl at pH 7.5, 50 mM NaCl, 5 mM MgCl₂, 1 mM dithiothreitol, 0.1 mg/ml BSA in a total volume of 0.4 ml at 37° C. for 5 hours. The reaction was stopped by adding 20 microliters 0.25 M EDTA and heated at 68° C. for 10 minutes. One hundred microliters 50% glycerol, 0.5% bromphenol blue was added and the sample was electrophoresed on a 1.2% agarose gel in 40 mM Tris, 20 mM NaAc, 2 mM EDTA (pH 7.8) at 40 V for 18 hours. The DNA bands on the gel were visualized under UV light after staining the gel in 1 microgram/ml ethidium bromide for 20 minutes. Slices of the gel containing DNA fragments between 1000 and 1300 bp were cut out and placed in a piece of dialysis tubing with 3 ml 20 mM Tris, 10 mM NaAc, 1 mM EDTA (pH 7.8) and the DNA was electroeluted from the gel with 20 V for 48 hours. The solution was removed from the dialysis tubing, the dialysis tubing and the gel slice were washed with 1 ml of the electroelution buffer, the solution and the wash were combined, and adjusted to 0.3 M NaAc using a 3 M stock. The DNA was precipitated by adding 3 volumes ethanol and redissolved in 40 microliters TE buffer. The purified EcoRl fragment (0.4 microgram) was joined to 0.75 micrograms EcoRl cleaved and phosphatase treated pUC9 with 2 units T4 DNA ligase in 50 mM Tris:HCl at pH 7.6, 10 mM MgCl₂, 10 mM dithiothreitol, 0.4 mM ATP in a total volume of 50 microliters at 12° C. for 16 hours. The ligated DNA solution was used to transform *E. coli* DH-1 (D. Hanahan, 1983, *J. Mol. Biol.*, 166, 577–580). To prepare the *E. coli* DH-1 for transformation, the bacteria were grown in 100 ml SOB media (2.0% Bacto-Tryptone, 0.5% yeast extract, 10 mM NaCl, 2.5 mM KCl, 10 mM MgCl₂, 10 MgSO₄) at 37° C. to an optical density of 0.5 at 550 nm, chilled on ice for 15 minutes, and harvested in sterile 50 ml conical polypropylene tubes by centrifugation (IEC floor model centrifuge) at 2000 rpm for 15 minutes at 4° C. The bacteria were suspended in 33 ml FSB (10 mM potassium acetate, 100 mM KCl, 45 mM MgCl₂, 10 mM CaCl₂, 10 mM CaCl₂, 3 mM hexamine cobalt(III) chloride, 10% glycerol, pH 6.4), incubated on ice for 15 minutes, and harvested by centrifugation as described above. The bacteria were suspended in 8 ml FSB and 0.425 ml aliquots of the suspension were placed in sterile 1.5 ml microcentrifuge tubes, frozen in liquid nitrogen, and stored at −70° C. until use. An aliquot of the frozen bacterial suspension was thawed on ice and 0.2 ml of the bacterial suspension was mixed with 15 microliters of the ligated DNA mixture described above and incubated on ice for 30 minutes. The tube containing the mixture was transferred to a 42° C. water bath for 2.5 minutes and placed on ice for 2 minutes. Then 0.8 ml SOC media (SOB media plus 20 mM glucose) was added and the tubes incubated at 37° C. with shaking for 1 hour. Bacteria were plated on 1% agar plates in LM broth (1% Bacto-Tryptone, 0.5% yeast extract, 10 mM NaCl, 10 mM MgSO₄) with 50 micrograms/ml ampicillin using a 3.5 ml top agar layer of 0.75% agar in SOB media with 50 micrograms/ml ampicillin. Recombinant plasmids in the transformed bacteria were screened for inserts about 1100 bp long and a representative clone was picked and called pT711.

The cDNA insert from lambda clone (22-1) with a 2100 bp insert was cleaved from the vector DNA by EcoRl into two fragments, one about 1100 bp long which is identical to the fragment cloned in pT711, and the other fragment about 1000 bp long. Each of these fragments contains part of the coding region for terminal transferase and together make up the entire coding sequence. To prepare the 1000 bp fragment from the recombinant lambda phage DNA, 50 micrograms recombinant phage DNA was digested with 4 units EcoRl nuclease in 100 mM Tris:HCl at pH 7.5, 50 mM NaCl, 5 mM MgCl₂, 1 mM dithiothreitol, 0.1 mg/ml BSA in a total volume of 0.25 ml at 37° C. for 60 minutes. The reaction was stopped by addition of 25 microliters 0.25 M EDTA, 25 microliters 5% SDS and heating the sample to 68° C. for 10 minutes. The DNA fragments were separated by electrophoresis on a 1% agarose gel and visualized under UV light after staining with 1 microgram/ml ethidium bromide. A slice of the gel containing the 1000 bp fragment was excised, minced, homogenized with phenol to extract DNA from agarose gel as described above. The aqueous DNA solution obtained was extracted twice with an equal volume of phenol:chloroform (1:1), five times with 1-butanol, once with chloroform:isoamyl alcohol (24:1), and adjusted to 0.5 M NaCl. The DNA was precipitated with 2.5 volumes ethanol and redissolved in 20 microliters TE buffer. The gel purified 1000 bp cDNA fragment and 0.5 micrograms EcoRl cleaved and phosphatase treated pUC8 DNA were ligated with 1.7 units T4 DNA ligase in 66 mM Tris:HCl at pH 7.6, 5 mM MgCl₂, 5 mM dithiothreitol, 1 mM ATP in a total volume of 50 microliters at 4° C. for 16 hours. The ligated DNA was used to transform *E. coli* HB-101. The *E. coli* HB-101 were prepared for transformation by the procedure using TFB solution as described above for *E. coli* DH-1. Two hundred microliters of the prepared bacteria suspension were transformed with 10 microliters of the ligated DNA by the procedure described above and plated on 1% agar plates made in L-broth with 50 microgram/ml ampicillin as described above. Recombinant plasmids in the transformed bacteria were screened for inserts about 1000 bp long and a representative clone was picked and called pT106.

Sequencing Procedures

To prepare DNA fragments for sequencing, overlapping deletions of the cloned cDNA fragments were made (M. Poncz, D. Solowiejczyk, M. Ballantine, E. Schwartz and S. Surrey, 1982, *Proc. Nat'l. Acad. Sci., USA*, 79, 4298-4302) by BAL-31 endonuclease digestion of the recombinant plasmids after cleavage of the plasmid DNA with either HindIII (clones in pBR322 or pUC9) or PstI (clones in pBR322). For HindIII cleavage 40 micrograms of plasmid DNA was digested with 40 units HindIII (BRL) in 50 mM NaCl, 50 mM Tris:HCl at pH 8.0, 10 -mM MgCl$_2$, 1 mM dithiothreitol, containing 0.1 mg/ml BSA in a total volume of 70 microliters for 5 hours at 37° C. The reaction was stopped with 7 microliters 0.25 M EDTA, 10 microliters 10% SDS, 10 microliters 3 M NaAc at pH 5.0, and extracted with 100 microliters phenol. The aqueous phase was removed, the phenol phase was washed with 50 microliters 0.3 M NaAc at pH 5, 5 mM EDTA, and the combined aqueous phases extracted twice with ether. The DNA was precipitated by adding 0.45 ml ethanol and cooling the mixture in a Dry Ice/ethanol bath (−70° C.) for 30 minutes. The precipitate was collected by centrifugation (Eppendorf microcentrifuge) for 10 minutes, washed with 75% and 95% ethanol, and dried under vacuum. For Pst I cleavage 50 micrograms plasmid DNA was digested with 100 units Pst I nuclease (BRL) in 20 mM Tris-HCl at pH 7.5, 50 mM (NH$_4$)$_2$SO$_4$, 10 mM MgCl$_2$, 1 mM dithiothreitol, 0.1 mg/ml BSA in a total volume of 100 microliters for 3 hours at 37° C. The reaction was stopped with 10 microliters 0.25 M EDTA, 14 microliters 10% SDS, 14 microliters 3 M NaAc, and extracted with 150 microliters phenol and ether, precipitated with ethanol at −20° C. for 16 hours, washed with ethanol solutions, and dried as described above.

For BAL-31 endonuclease digestion the HindIII or Pst I cleaved DNA was dissolved in 0.1 ml 12 mM CaCl$_2$, 12 mM MgCl$_2$, 600 mM NaCl, 20 mM Tris:HCl at pH 8.0, 1 mM EDTA, 0.25 mg/ml BSA. BAL-31 nuclease (New England Biolabs), 4-6 units, was added and the reaction mixture incubated at 30° C. An 8 microliter aliquot was removed every 2 minutes and added to 3 microliters 0.1 M EGTA. The sizes of the digested DNAs were determined by agarose gel electrophoresis and fractions containing appropriate sizes were pooled. The DNA ends were repaired with the large fragment of *E. coli* DNA polymerase I at 200 units/ml in 50 mM Tris:HCl at pH 7.5, 5 mM MgCl$_2$, 10 mM 2-mercaptoethanol, 0.4 mM each of dATP, dCTP, dGTP and dTTP, and 50 micrograms/ml BSA in a total volume of 25 microliters at 30° C. for 30 minutes. The reaction was stopped with EDTA and extracted with phenol and the DNA was precipitated with ethanol and collected by centrifugation as described above. Phosphorylated HindIII linkers d(CCAAGCTTGG) (Collaborative Research) 0.1 mg/ml were ligated to the DNA in 66 mM Tris:HCl at pH 7.6, 5 mM MgCl$_2$, 5 mM dithiothreitol, 1 mM ATP, 200 units/ml T4 DNA ligase in a total volume of 30 microliters at 4° C. for 16 hours. The mixtures were heated at 70° C. for 15 minutes to inactivate the DNA ligase and the DNA was digested with HindIII and EcoRl by adding 6 microliters 100 mM Tris-HCl, pH 7.5, 50 mM NaCl, 5 mM MgCl$_2$, 6 microliters 10 mM dithiothreitol, 6 microliters 1 mg/ml BSA, 40 units EcoRl and 45 units HindIII (BRL) in a total volume of 60 microliters and re-incubated for 4 hours at 37° C. The reactions were stopped with 6 microliters 0.25 M EDTA, 6 microliters 10% SDS, 7 microliters 20% Ficoll with bromphenol blue and xylene cyanol marker dyes to 0.0125% and the DNA fragments were separated by electrophoresis on a 2% agarose gel in 40 mM Tris, 20 mM NaAc, 2 mM EDTA, pH 7.8. DNA fragments smaller than the initial DNA insert and larger than 100 bp were purified from the gel and ligated to HindIII and EcoRl cleaved plasmid pUC8 using T4 DNA ligase as described above. The recombinant plasmids were transfected into *E. coli* strain DH-1 (D. Hanahan, 1983, *J. Mol. Biol.*, 166, 577–580).

Single stranded templates for sequencing by the dideoxy chain termination method were made from plasmid DNA by cleavage with restriction endonuclease followed by digestion with exonuclease III (A. J. H. Smith, 1979, *Nucleic Acids Res.*, 6, 831-847). The recombinant plasmids pT16, −17, −18, −19 with inserts in the EcoRl site of pBR322 DNA were digested (5 micrograms plasmid DNA) with 10 units HindIII (BRL) in 50 mM Tris:HCl at pH 7.6, 10 mM MgCl$_2$, 10 mM DTT, 50 mM KCl, 0.1 mg/ml BSA in a total volume of 15 microliters for 3 hours at 37° C. The buffer was adjusted with 6 microliters 0.66 M Tris:HCl at pH 8, 770 mM NaCl, 50 mM MgCl$_2$, 100 mM dithiothreitol and 38 microliters water and the DNA was digested with 75 units exonuclease III for 3 hours at 37° C. The reaction was stopped with 15 microliters 0.25 M EDTA and 8 microliters 3 M NaAc at pH 8, extracted with phenol and ether, precipitated with ethanol, and redissolved in 32 microliters water as described above. These preparations were sequenced using the pBR322 EcoRl primer, d(GTATCACGAGGCCCTT) (P-L Biochemicals).

For sequencing the opposite end of the inserts in pT16, −17, −18, −19, ten micrograms of plasmid DNA was cleaved with 24 units Pst I in 20 mM Tris:HCl at pH 7.6, 10 mM MgCl$_2$, 50 mM NH$_4$Cl, 1 mM dithiothreitol, 0.1 mg/ml BSA in a total volume of 30 microliters for 4 hours at 37° C. The reaction was stopped by adding 3 microliters 0.25 M EDTA, 3.5 microliters 3 M NaAc, extracted with phenol and ether, precipitated with ethanol, and redissolved in 100 microliters 12 mM CaCl$_2$, 12 mM MgCl$_2$, 20 mM NaCl, 20 mM Tris:HCl at pH 8, 1 mM EDTA, 0.25 mg/ml BSA and digested with 1.5 units BAL-31 nuclease for 4 minutes at 30° C. The reactions were stopped with 30 microliters 0.1 M EGTA, 15 microliters 0.25 M EDTA, 5 microliters 3 M NaAc, extracted with phenol and ether, precipitated with ethanol as described above, and redissolved in 60 microliters 78.5 mM Tris:HCl at pH 7.9, 7.5 mM MgCl$_2$, 12.5 mM dithiothreitol, 7.5 mM KCl, 77 mM NaCl and digested with 75 units exonuclease III for 3 hours at 37° C. The exonuclease III reaction was stopped and the DNA precipitated with ethanol, collected, washed, dried, and dissolved in water as described above. These preparations were sequenced using the pBR322 HindIII primer, d(GCAATTTAACTGTGAT) (P-L Biochemicals).

Deletion fragments derived from pT17 which were cloned between the EcoRl and HindIII sites of pUC8 were digested with 10 units EcoRl using the same conditions described above for the HindIII digestion of pT16. The EcoRl cleaved DNA was digested with exonuclease III as described above, dissolved in 16 microliters water, and sequenced with the M13 15-base sequencing primer (BRL). The cDNA fragment in pT711 which was cloned in the EcoRl site of pUC9 was digested with HindIII and exonuclease III as described above and sequenced with the M13 15-base sequencing primer.

The cDNA fragments in pT106 which were cloned in the EcoRl site of pUC8 were digested with HindIII and exonuclease III as described above and sequenced with the M13 reverse sequencing primer.

Deletion fragments derived from pT106 which were cloned between the EcoRI and HindIII sites of pUC8 were digested with 10 units EcoRl using the same conditions described above for the HindIII digestion of pT16. The EcoRl cleaved DNA was digested with exonuclease III as described above, dissolved in 16 microliters water, and sequenced using the M13 15-base sequencing primer.

The single stranded templates were sequenced by the dideoxy chain termination method (F. Sanger, S. Nicklen and A. R. Coulson, 1977, *Proc. Nat'l. Acad. Sci. USA*, 74, 5463-5467) using reagents and instructions from the M13 sequencing kit from BRL.

Eight microliters of the exonuclease III digested DNA samples described above were mixed with 4 nanograms of the appropriate primer and adjusted to 6.4 mM Tris:HCl at pH 7.5, 6.4 mM $MgCl_2$, 45.5. mM NaCl in a final volume of 11 microliters in a 400 microliter microcentrifuge tube. The tubes were capped tightly, heated to 100° C. in a boiling water bath for 5 minutes, removed and the DNA was allowed to anneal 45 minutes by slow equilibration to room temperature. To the annealed template primer mixture was added 1 microliter 100 mM dithiothreitol, 2.5 ( 1 microliters alpha-$^{32}$P-dATP (New England Nuclear, 0.0125 mM, 800-200 Ci/mmole), and 1 microliter large fragment of *E. coli* DNA polymerase I (1 unit). Three microliters of the primer:template:$^{32}$P-dATP:enzyme mixture was mixed with 2 microliters buffer and nucleoside triphosphates to give the final four sequencing reactions for A, C, G, and T. The buffer concentration in all four sequencing reactions was 7 mM Tris:HCl at pH 7.5, 7 mM $MgCl_2$, 50 mM NaCl and the nucleoside triphosphate concentrations were as follows: A reaction, 0.025 mM dCTP, 0.025 mM dGTP, 0.025 mM dTTP, 0.1 mM ddATP; C reaction, 0.0016 mM dCTP, 0.033 mM dGTP, 0.033 mM dTTP, 0.05 mM ddCTP; G reaction, 0.033 mM dCTP, 0.0016 mM dGTP, 0.033 mM dTTP, 0.1 mM ddGTP; and T reaction, 0.033 mM dCTP, 0.033 mM dGTP, 0.0016 mM dTTP, 0.2 mM ddTTP. The reaction mixtures were incubated at 30° C. for 5 minutes and 42° C. for 15 minutes, 1 microliter of 0.5 mM dATP was added to each reaction and this mixture was incubated at 42° C. for 15 minutes. The reactions were stopped by adding 10 microliters 95% formamide, 10 mM EDTA, 0.1% bromphenol blue, 0.1% xylene cyanol. The samples were heated in a boiling water bath for 2 minutes and 2 microliter aliquots were electrophoresed on 8% polyacrylamide gels (33×40×0.04 cm) with 8 M urea in 75 mM Tris, 50 mM boric acid, 1.5 mM EDTA at 2000 V for 2-6 hours. DNA fragments terminated by each of the dideoxynucleotides were detected by autoradiographic exposure on Kodak XAR-5 film. The complete cDNA sequence determined is shown in FIG. 2.

TdT Expression in pUC19

Translation of the TdT messenger RNA starts at the nucleotides that correspond to the ATG at position No. 329 of the cDNA (FIG. 2). This is the initiation codon that codes for the amino acid methionine (Met). A recognition site for the restriction endonuclease BamHI (GGATCC) immediately follows the initiation codon in the TdT cDNA sequence in pT106, and can be used to split this fragment of cDNA into coding and noncoding regions.

...ATGGATCC...

Expression of the human TdT in *E. coli* can be accomplished by joining the coding portion of the TdT cDNA to an *E. coli* gene if the two coding regions are in the same reading frame. The vector pUC19, which uses the lac expression system, was used but there are numerous other bacterial and viral genes that can be used. pUC19 is a plasmid that carriers the gene for resistance to the antibiotic ampicillin, an origin of replication, and a portion of the *E. coli* lac operon with the promoter, operator, and some of the coding region of the lac Z gene, called the lac Z' gene (C. Yanisch-Perron, J. Viera, and J. Messing, 1985, *Gene*, 33, 103-119). Near the 5' end of the lac Z' gene there are restriction endonuclease sites for BamHI and EcoRl. When the TdT cDNA and the lac Z' coding region of pUC19 are joined at the BamHI sites the protein coding portion of the TdT cDNA is placed in the same reading frame as the 5'-end of the lac Z' gene. In this modified gene, transcription (synthesis of RNA) begins at the promoter of the lac operon in the plasmid, translates a small segment of the lac Z' gene, and continues through the inserted TdT 16 cDNA. The product RNA contains the ribosome binding sequence from the lac operon required to start the translation (conversion of nucleotide sequence to an amino acid sequence) of the RNA on the *E. coli* ribosomes. The hybrid protein that is produced contains 15 amino acids from the lac Z' coding region of the plasmid pUC19 followed by the amino acids coded by the insert of the TdT cDNA.

To construct this hybrid gene a BamHI-EcoRl fragment from pUC19 was joined to a BamHI-EcoRl fragment of the TdT cDNA from pT106 and an EcoRl fragment of the TdT cDNA from pT711. Ten micrograms of pUC19 DNA (original stock from BRL in *E. coli* host strain JM83) was digested with 20 units of EcoRl (BRL) in 50 mM Tris:HCl at pH 7.6, 50 mM NaCl, 10 mM $MgCl_2$, 1 mM dithiothreitol, 0.1 mg/ml BSA in a total volume of 40 microliters at 37° C. for 2 hours. The reaction was stopped by adding EDTA to a final concentration of 12.5 mM. NaAc (3 M) was added to a final concentration of 0.3 M and the mixture was extracted with 40 microliters phenol:chloroform (1:1). The aqueous phase was removed and the organic layer was extracted with 0.3 M NaAc. The aqueous layers were combined and the DNA was precipitated with 3 volumes of ethanol at −20° C. for 16 hours. The precipitate was collected by centrifugation (Eppendorf microcentrifuge) for 10 minutes, washed with cold 75% ethanol, dried by vacuum, and dissolved in 20 microliters of 50 mM Tris:HCl at pH 8.0, 1 mM EDTA. Calf intestinal phosphatase, 5 units (Boehringer Mannheim), was added and the mixture incubated at 37° C. for 60 minutes. The reaction was stopped by adding 2.5 microliters 0.25 M EDTA, 2.5 microliters 10% SDS, 2.5 microliters 3 M NaAc and heating to 68° C. for 10 minutes. The mixture was extracted with phenol:chloroform (1:1), precipitated with ethanol, and redissolved in 10 microliters of TE buffer as described above. Ten microliters 4 M ammonium acetate was added and the DNA was precipitated with 2 volumes of ethanol at −70° C. for 30 minutes, collected by centrifugation, washed with 75% ethanol, dried under vacuum, and redissolved in 18 microliters TE buffer. The DNA was digested with 18 units of BamHI (BRL) in 100 mM NaCl, 20 mM Tris:HCl at pH 7.6, 7 mM MgCl$_2$, 1 mM dithiothreitol, 0.1 mg/ml BSA, 3.3 mM potassium phosphate in a total volume of 30 microliters at 37° C. for 2.5 hours. The reaction was stopped by adding 6 microliters 14% Ficoll (Pharmacia), 0.15% bromphenol blue and xylene cyanol, and 75 mM EDTA.

Plasmid DNA pT106 was treated with EcoRl, phosphatase, and BamHI exactly as described for pUC19 above.

Plasmid DNA pT711 (10 micrograms) was digested with 20 units of EcoRl (BRL) in 50 mM Tris:HCl at pH 7.6, 50 mM NaCl, 10 mM MgCl$_2$, 1 mM dithiothreitol, 0.1 mg/ml BSA in a total volume of 40 microliters at 37° C. for 2 hours. The reaction was stopped by adding 4 microliters 0.25 M EDTA and 4.5 microliters 3 M NaAc and extracted with phenol:chloroform (1:1), precipitated with ethanol, and redissolved in 20 microliters TE buffer. The sample was adjusted to 2% Ficoll and 0.05% bromphenol blue and xylene cyanol before electrophoresis.

The DNA fragments from the above three digestions were loaded onto separate wells of a horizontal 1% agarose (BRL) gel in 40 mM Tris, 20 mM NaAc, 2 mM EDTA (pH 7.8) and subjected to electrophoresis at 25 V for 13 hours. The 2700 bp EcoRl-BamHI pUC19 fragment, the 634 bp EcoRl-BamHI fragment from pT106 and the 1103 bp EcoRl fragment from pT711 were extracted from the gel (D. S. Holmes, Biotechniques, pp 66-67, March/April 1984). A gel slice containing each of the DNA fragments was minced thoroughly and then mixed vigorously with an equal volume of phenol. The mixture was frozen at −70° C. in a dry-ice/ethanol bath for 10 minutes and centrifuged (Eppendorf microcentrifuge) for 15 minutes at room temperature. The supernatant was removed and saved. One fourth volume of distilled water was added to the phenol/agarose phase, mixed vigorously, frozen at −70° C. for 10 minutes, and centrifuged for 10 minutes. The supernatant was removed and added to the first supernatant. The combined supernatants were extracted twice with an equal volume of phenol leaving the white interface with the phenol layer. The aqueous supernatant was extracted twice with an equal volume of ether and adjusted to a final concentration of 0.3 M NaAc using a 3 M stock solution. DNA was precipitated with ethanol and redissolved in 50 microliters of TE buffer. Equal molar amounts of the EcoRl-BamHI pUC19 fragment, the 1103 bp pT711 EcoRl fragment, and the 634 bp EcoRl-BamHI pT106 isolated from agarose gels as described above were joined together with 1.7 units T4 DNA ligase (Collaborative Research) in 50 mM Tris:HCl at pH 7.6, 10 mM MgCl$_2$, 10 mM dithiothreitol, 0.4 mM ATP in a final volume of 20 microliters at 14° C. for 16 hours. This ligation procedure produces a mixture of DNA products of which only some will produce polypeptides related to TdT.

The DNA mixture was used to transform *E. coli* strain HB101 (T. Maniatis, *et al., Molecular Cloning,* Cold Spring Harbor Laboratory, 1982). A 100 ml culture of HB101 in L-broth was started with 0.5 ml of a fresh overnight culture and grown at 37° C. with shaking until the optical density reached 0.5 (aproximately 5×10$^8$ cells/ml). The culture was transferred to sterile 50 ml screw cap centrifuge tubes and placed on ice for 15 minutes. The cells were harvested by centrifugation at 2000 rpm in an SS-34 rotor (Sorvall) for 15 minutes at 4° C. The cell pellets were washed with 5 ml cold TE buffer and centrifuged at 2000 rpm for 15 minutes at 4° C. The supernatant was decanted and the cell pellets resuspended in a total volume of 10 ml 75 mM CaCl$_2$ and incubated on ice for 15 minutes. The cells are now competent to take up DNA added to the suspension and can be used immediately or adjusted to 16% glycerol using a sterile 80% glycerol stock, frozen in dry-ice/ethanol bath, and stored at −70° C. until use. Six microliters of the ligation reaction (above) was placed in a Falcon 3033 tube on ice. Competent *E. coli* HB101 cells (0.2 ml) were added to this tube and the mixture was incubated for 30 minutes on ice. The tube was transferred to a 42° C. water bath for 2.5 minutes and then transferred back to ice for 2 minutes. L-broth (0.8 ml) was added and the culture was incubated at 37° C. with shaking for 1 hour. The cells were plated on 2X L-broth agar plates with 0.1 mg/ml ampicillin using L-broth top agar.

The plasmid DNAs from the resulting transformed cells were prepared by the method of Holmes and Quigley (D. S. Holmes and M. Quigley, 1981, *Anal., Biochem.,* 114, 193–197) and analyzed for the size of the recombinant plasmid DNA on 1% agarose gels. Two sizes of recombinant molecules were obtained having inserts of either 634- or 1737-bp. The recombinants with the 634 bp insert result from joining the 634 bp EcoRl-BamHI fragment from pT106 to pUC19 and a representative of this class was called pT201. The recombinants with the 1737 bp insert result from joining the 634 bp EcoRl-BamHI fragment from pT106 and the 1103 bp EcoRl fragment from pT711 to pUC19. The 1103 bp EcoRl fragment from pT711 can be present in two orientations, only one of which will give the continuous coding region required for expression of full length TdT protein. A representative of the class of recombinants with the 1103 bp fragment in the proper orientation to regenerate the complete coding region was called pT223 and a representative of the class with the 1103 bp fragment in the opposite orientation was called pT226. The correct assignment of the orientations in these recombinants was determined by restriction endonuclease digestions of the plasmid DNA. Approximately 0.5 microgram samples of plasmid DNA were digested with either 10 units AluI or 10 units HaeIII (BRD) in 50 mM NaCl, 6 mM Tris:HCl at pH 7.5, 6 mM MgCl$_2$, 1 mM ditheiothreitol, 0.1 mg/ml BSA a total volume of 10 microliters at 37° C. for 3 hours. The reaction was stopped by adding 1 microliter 0.25 M EDTA and 1 microlilter of 20% Ficoll, bromphenol blue, xylene cyanol solution, and the fragments were separated on an 8% polyacrylamide gel in 40 mM Tris, 20 mM sodium acetate, 2 mM EDTA (pH 7.8). The DNA fragments were observed under UV light after staining the gel in 1 microgram/ml ethidium bromide solution.

The predicted sizes of the fragments arising from (i.e. containing some portion of) the insert regions in the recombinant plasmids are characteristic for each of the three classes of recombinants. The characteristic AluI fragments are 188- and 148bp for pT201; 188-, 133-, and 576-bp for pT223; and 188-, 532-, and 169-bp for pT226. The characteristic HaeIII fragments are 294- and 236- bp for pT201; 294-, 516-, and 33-bp for pT223; and 294-, 249-, 516-, and 300-bp for pT226. The restriction enzyme fragment analysis showed that pT223 contains the terminal transferase sequences from pT106 and pT711 in the proper orientation in relation to the lac Z' promoter sequences in pUC19.

*E. coli* carrying the recombinant plasmids were screened for the production of material that reacts with antibodies to TdT (D. M. Helfman, J. R. Feramisco, J. C. Fiddes, J. C., G. P. Thomas, and S. H. Hughes, S. H., 1983, *Proc. Nat'l. Acad. Sci. USA*, 80, 31–35). Bacteria were grown as streaks on sterile nitrocellulose filters (Schleicher & Schuell) on 100 mm square L-broth agar plates with 0.1 mg/ml ampicillin for 5 hours at 37° C. The filters with the bacteria were transferred onto L-broth/agar/ampicillin plates that had a top overlay of 3.5 ml L-broth, 0.75% agar, 0.3 mM IPTG and were incubated for an additional 3 hours at 37° C. The bacteria were lysed on the filter by removing the filter from the plate and hanging it in an atmosphere of chloroform for 15 minutes. Filters were then washed (10 ml per filter) with 50 mM Tris:HCl at pH 7.5, 150 mM NaCl, 5 mM $MgCl_2$, 3% BSA, 40 microgram/ml lysozyme, 1 microgram/ml pancreatic DNase for 16 hours at room temperature. The filter was washed three times for five minutes each with TBS and blocked with 20% FCS in TBS for 1 hour. The filters were soaked in 2 micrograms/ml of affinity purified rabbit antibody to TdT in 20% FCS in TBS for 1 hour, washed with TBS five times for 5 minutes each, reacted with an 100 micrograms/ml of goat antibodies to rabbit IgG in 20% FCS in TBS for 1 hour, washed with TBS five times for 5 minutes each, reacted with 1/250 dilution of rabbit anti-horseradish peroxidase-peroxidase complex (Accurate Chemicals) in 20% FCS in TBS for 1 hour, washed with TBS five times for 5 minutes each, and incubated in 0.5 mg/ml 4-chloro-1-naphthol, 0.001% $H_2O_2$ in TBS for 30 minutes. Peptides that react with the rabbit antibody to TdT develop a blue color under these conditions. Bacteria harboring the plasmid pT223 produce peptides that react with the antibodies to terminal transferase while bacteria with the plasmids pT201 or pT226 did not produce immunoreactive material. The structure of the pUC19(BamHI-EcoR1)/pT223 molecule is shown in FIG. 1.

EXAMPLES

EXAMPLE 1

Hybridization of Human TdT cDNA to Other DNAs

Chromosomal DNA from human fibroblasts calf thymus gland, mouse liver, rainbow trout sperm, Tetrahymena sp. (a protozoan), *Diploccoccus pneuomina* (a bacterium) and DNA prepared from pBR322 were obtained by standard methods for isolation of high molecular weight DNA. Serial dilutions of each DNA solution containing 10 to 10,000 nanograms were applied to a sheet of nitrocellulose, dried and hybridized with 32P-labelled pT106 and pT711 inserts. After hybridization and washing the nitrocellulose sheet was exposed to X-ray film.

A positive hybridization is detected as intense exposure of the X-ray film resulting from the formation of a hybridization complex with those DNA samples that contain sequences related to the radioactive hybridization probe. This experiment showed that the pT711 and pT106 sequences (probes) do not hybridize to pBR322 DNA (the negative control), or to the Tetrahymena sp. or *Diploccoccus pneumoniae* DNA. On the other hand, strong hybridization was observed with human fibroblast DNA (the positive control), mouse liver, calf thymus, and rainbow trout sperm DNA. Thus our human DNA probes detect complementary sequences in animals as low as fishes, but not in protozoal or bacterial cells. This demonstrates that the TdT sequence is conserved in lower animals and can be detected and therefore isolated using the TdT DNA cDNA sequence we have discovered.

EXAMPLE 2

Hybridization of Human TdT cDNA to Quantitate TdT RNA Expression

Total poly (A) RNAs were prepared from human lymphoblastoid cells KM-3 (TdT-positive) and human lymphoblastoid cells RAMOS-1 (TdT-negative), and serial dilutions containing 20 nanograms to 250 nanograms was applied to a sheet of nitrocellulose. The nitrocellulose sheet was dried, hybridized with $^{32}P$-nick-translated insert of pT106 and pT711, washed, and exposed to X-ray film. The amounts of RNA hybridizing with the probes in each sample was quantitated by densitometer tracing of the intensities of "spots" on the X-ray film. A standard curve (amount of TdT mRNA vs the intensities of the spots) was established from the KM-3 RNA dilutions. No hybridization was detected with RAMOS-1 RNA dilutions as expected for the negative control. The level of TdT RNA expression can thus be estimated for any unknown crude cytoplasmic RNA sample (B. A. White and F. C. Bancroft, 1982, *J. Biol. Chem.*, 257, 8569–8572).

EXAMPLE 3

Expression of Human TdT in *Escherichia coli*

Our initial discovery of the recombinant plasmid containing human TdT sequence required detection of the protein sequence of TdT in bacterial plasmid systems using specific immunological methods. To demonstrate that active human enzyme is produced in bacterial cells in the presence of plasmids containing TdT DNA sequence in the proper orientation and under appropriate controls we selected a plasmid variant called pT226 in which the pT711 insert at the EcoR1 site was in the opposite orientation. This plasmid might produce a protein that can be recognized by antibody but would contain no enzyme activity. Plasmid pT223 should produce full length TdT protein sequence and might possess enzyme activity in addition to immunological reactivity.

Five *E. coli* cultures containing or lacking various plasmids were grown up, extracts were made and the extracts were assayed for TdT activity. The results in Table I were produced.

TABLE I

| *E. coli* Cells | Terminal Transferase Activity (units/mg. protein) |
| --- | --- |
| HB 101 | 2.3 |
| HB 101 with pUC19 | 2.0 |
| HB 101 with pT201 | 1.7 |
| HB 101 with pT223 | 207 |
| HB 101 with pT226 | 0.5 |

Enzyme activity less than 2.5 units/mg protein is considered the result of other kinds of deoxynucleotide polymerizing activity in the bacterial extracts. The presence of 200 units/mg protein in the HB 101/pT223 extract is highly significant, indicating that the presence of pT223 inside the bacterial cells leads to production of an enzyme foreign to this cell type.

Larger cultures of HB 101/pT223, e.g. 100 ml to 1000 ml, were then grown up and extracts of the bacterial cells were made. These extracts were passed over a monoclonal immuno-affinity column that contained mouse antibody to human TdT covalently coupled to Protein A Sepharose. The column was washed with buffer solution and then the specifically absorbed protein was eluted with 3.5 M magnesium chloride buffered with 50 mM Tris:HCl buffer at pH 8.0. The magnesium chloride was dialyzed away and the resultant solution was assayed for protein and TdT activity. The assay showed about 25,000 units of TdT activity per mg of specific protein. This demonstrates that the protein made in the bacterial cells under the influence of pT223 makes a human TdT protein that contains TdT activity, and that this protein can be isolated from the bacterial proteins with immuno-affinity columns. The enzyme purified from the E. coli HB 101/pT223 extracts was analyzed for size on denaturing electrophoresis gels and was shown to have the size predicted from the pT223 construct (about 60 kDa).

EXAMPLE 4

Enzyme Activity Expressed from Deletion Plasmids

The recombinant plasmid pT223 was cleaved with Pstl and BamH1 and TdT cDNA sequences were removed sequentially from this linearized plasmid with exonuclease III and S1 nuclease. This procedure leaves the lac Z' promoter on the plasmid intact and removes DNA only from the part of the TdT cDNA coding for the amino-terminus of the protein, resulting in a shorter TdT coding region on the cDNA. These plasmids were re-circularized by the action of T4 DNA ligase and used to transform E. coli HB101 cells. Bacteria transformed with these modified recombinant plasmids were screened for the size of the insert in the plasmids and for the ability to produce proteins that react with antibodies to TdT. A large number of plasmids containing parts of the TdT cDNA, as judged by the sizes of the recombinant plasmids, were able to direct the synthesis of proteins that were immunoreactive. Extracts of bacteria with these plasmids were assayed and some were found to have TdT activity. To determine the sizes of the proteins produced bacterial extracts were separated on SDS polyacrylamide gels, transferred to nitrocellulose and reacted with antibodies to TdT. Proteins encoded by the modified cDNA fragments were found to be smaller than the protein made by the original plasmid pT223. This demonstrates that the cDNA sequences of TdT can be manipulated to produce in bacteria altered peptides that retain immunologic reactivity and enzymatic activity of the TdT protein sequence.

Overall Conclusions

In this invention, we have demonstrated that we have isolated molecules containing the coding sequence for human TdT. Furthermore, we have determined the complete coding sequence of human TdT protein as well as 5'-upstream and 3'-downstream leading and trailing sequences present in the TdT cDNA. We have demonstrated the universal conservation of this sequence in animals from humans to fishes.

When the sequence, or parts thereof, discovered by us is placed in proper orientation to control sequence elements from other sources causing the expression of this sequence, through reactivity and/or enzyme activity are produced. This discovery provides a completely new method for producing human TdT-related molecules.

DNA Molecules on Deposit with the American Type Culture Collection (ATCC)

DNA molecules prepared by the processes described herein are exemplified by E. coli strains containing the plasmids noted below, deposited with ATCC on Apr. 18, 1986 and identified as follows:
Strain DH1 pUC9 (EcoRl)/pT711 (ATCC No. 67094)
Strain HB101 pUC8 (EcoRl)/pT106 (ATCC No. 67093)
Strain HB101 pUC19 (BamH1-EcoRl)/pT223 (ATCC No. 67095)

The conclusions drawn and subject matter claimed in this application can be reproduced and demonstrated using the plasmid DNA molecules contained in these strains of bacteria.

We claim:
1. A modified DNA vector, comprising:
   a. the DNA vector, and
   b. a segment of DNA containing an expression control sequence operably linked to a nucleotide sequence selected from the group consisting of,
      1. The pT223/BamH1/EcoRl insert containing the complete coding sequence of the human terminal deoxynucleotidyl transferase (minus N-terminal methionine),
      2. DNA sequences that code for the expression of human terminal deoxynucleotidyl transferase described in b.(1) herein, with or without N-terminal methionine, and
      3. DNA sequences that hybridize to the pT223/BamHI/Eco R1 DNA sequence and encode a polypeptide having human terminal deopxynucleotidyl transferase activity.
2. The modified DNA vector of claim 1 wherein the DAN sequence is the pT223/BamHI/EcoRl insert containing the complete coding sequence of the human terminal deoxynucleotidyl transferase (minus N-terminal methionine).
3. The modified DNA vector of claim 1 wherein the DNA sequence is one that codes for the expression of the DNA sequence pT223/BamHI/EcoRl insert containing the complete coding sequence of the human terminal deoxynucleotidyl transferase which may contain a N-terminal methionine.
4. The modified DNA vector of claim 1 wherein the molecule comprises a cloning vehicle having at least one restriction endonuclease recognition site, said DNA sequence being inserted at one of said recognition sites or between two such sites.
5. The modified DNA vector according to claim 1 wherein the expression control sequence is selected from the group consisting of a lac system, trp system, major operator and promoter regions of phage lambda, the control region of fd coat protein, and other sequences which control the expression of genes of prokaryotic or eukayotic cells and their viruses.
6. A unicellular host transformed with at least one copy of the modified vector, consisting of:
   a. the DNA vector and
   b. a segment of DNA containing an expression control sequence operably linked to a nucleotide sequence selected from the group consisting of,
      1. the pT223/BamH1/EcoRl insert containing the complete coding sequence of the human terminal deoxynucleotidyl transferase (minus N-terminal methionine),
2. The DNA sequences that code for the expression of human terminal deoxynucleotidyl transferase described in b. (1) herein, with or without N-terminal methionine, and
3. DNA sequences that hybridize to the pT223/BamHI/Eco R1 DNA sequence and encode a polypeptide having human terminal deoxynucleotidyl transferase activity.

7. The transformed host according to claim 6 wherein the host is selected from the group consisting of *E. coli* DH1 (pUC9(EcoRl)/pt711) (ATTC No. 67094), *E. coli* HB101 (pUC8 (EcoRl)/pT106), (ATTC No. 67094), *E. coli* HB101 (pUC19 (BamH1-EcoRl)/pT106), (ATTC No. 67093), and *E. coli* HB101 (pUC19 (BamH1-EcoRl)/pT223) (ATTC No. 67095).

8. The transformed host according to claim 6 wherien the vector is a microbial or yeast plasmid or, a virus.

9. The transformed host according to claim 8 wherein the virus is selected from the group consisting of bacteriophage, animal virus, plant virus, and insect virus.

10. An isolated DNA sequence encoding human termianal deoxynucleotidyl transferase having the following nucleotide sequence:

| | | | Composition: | 595 A, | 405 C, | 542 G, | 526 T | Length: | 2068 |
|---|---|---|---|---|---|---|---|---|---|
| | | 10 | 20 | 30 | 40 | 50 | 60 |
| 1 | TCATTGGGTG | ATTGATTTCT | ATGCTCCTTG | GTGTGGACCT | TGCCAGAATT | TTGCTCCAGA |
| 61 | ATTTGAGCTC | TTGGCTAGGA | TGATTAAAGG | AAAAGTGAAA | GCTGGAAAAG | TAGACTGTCA |
| 121 | GGCTTATGCT | CAGACATGCC | AGAAAGCTGG | GATCAGGGCC | TATCCAACTG | TTAAGTTTTA |
| 181 | TTTCTACGAA | AGAGCAAAGA | GAAATTTTCA | AGAAGAGGGG | GGGGGGGGGG | CCCCCCCCAA |
| 241 | AAACCCTTCG | TGTAGGAGGG | TGGCAGTCTC | CCTCCCTTCT | GGAGACACCA | CCAGATGGGC |
| 301 | CAGCCAGAGG | CAGCAGCAGC | CTCTTCCCAT | GGATCCACCA | CGAGCGTCCC | ACTTGAGCCC |
| 361 | TCGGAAGAAG | AGACCCCGGC | AGACGGGTGC | CTTGATGGCC | TCCTCTCCTC | AAGACATCAA |
| 421 | ATTTCAAGAT | TTGGTCGTCT | TCATTTTGGA | GAAGAAAATG | GGAACCACCC | GCAGAGCGTT |
| 481 | CCTCATGGAG | CTGGCCCGCA | GGAAAGGGTT | CAGGGTTGAA | AATGAGCTCA | GTGATTCTGT |
| 541 | CACCCACATT | GTAGCAGAGA | ACAACTCGGG | TTCGGATGTT | CTGGAGTGGC | TTCAAGCACA |
| 601 | GAAAGTACAA | GTCAGCTCAC | AACCAGAGCT | CCTCGATGTC | TCCTGGCTGA | TCGAATGCAT |
| 661 | AGGAGCAGGG | AAACCGGTGG | AAATGACAGG | AAAACACCAG | CTTTGTGTGA | GAAGAGACTA |
| 721 | TTCAGATAGC | ACCAACCCAG | GCCCCCCGAA | GACTCCACCA | ATTGCTGTAC | AAAAGATCTC |
| 781 | CCAGTATGCG | TGTCAGAGAA | GAACCACTTT | AAACAACTGT | AACCAGATAT | TCACGGATGC |
| 841 | CTTTGATATA | CTGGCTGAAA | ACTGTGAGTT | TAGAGAAAAT | GAAGACTCCT | GTGTGACATT |
| 901 | TATGAGAGCA | GCTTCTGTAT | TGAAATCTCT | GCCATTCACA | ATCATCAGTA | TGAAGGACAC |
| 961 | AGAAGGAATT | CCCTGCCTGG | GGTCCAAGGT | GAAGGGTATC | ATAGAGGAGA | TTATTGAAGA |
| 1021 | TGGAGAAAGT | TCTGAAGTTA | AAGCTGTGTT | AAATGATGAA | CGATATCAAT | CCTTCAAACT |
| 1081 | CTTTACTTCT | GTATTTGGAG | TGGGGCTGAA | GACTTCTGAG | AAGTGGTTCA | GGATGGGTTT |
| 1141 | CAGAACTCTG | AGTAAAGTAA | GGTCGGACAA | AAGCCTGAAA | TTTACACGAA | TGCAGAAAGC |
| 1201 | AGGATTTCTG | TATTATGAAG | ACCTTGTCAG | CTGTGTGACC | AGGGCAGAAG | CAGAGGCCGT |
| 1261 | CAGTGTGCTG | GTTAAAGAGG | CTGTCTGGGC | ATTTCTTCCG | GATGCTTTCG | TCACCATGAC |
| 1321 | AGGAGGGTTC | CGGAGGGGTA | AGAAGATGGG | GCATGATGTA | GATTTTTTAA | TTACCAGCCC |
| 1381 | AGGATCAACA | GAGGATGAAG | AGCAACTTTT | ACAGAAAGTG | ATGAACTTAT | GGGAAAAGAA |
| 1441 | GGGATTACTT | TTATATTATG | ACCTTGTGGA | GTCAACATTT | GAAAAGCTCA | GGTTGCCTAG |
| 1501 | CAGGAAGGTT | GATGCTTTGG | ATCATTTTCA | AAAGTGCTTT | CTGATTTTCA | AATTGCCTCG |
| 1561 | TCAAAGAGTG | GACAGTGACC | AGTCCAGCTG | GCAGGAAGGA | AAGACCTGGA | AGGCCATCCG |
| 1621 | TGTGGATTTA | GTTCTGTGCC | CCTACGACTG | TCGTGCCTTT | GCCCTGTTGG | GATGGACTGG |
| 1681 | CTCCCGGTTT | GAGAGAGACC | TCCGGCGCTA | TGCCACACAT | GAGCGGAAGA | TGATTCTGGA |
| 1741 | TAACCATGCT | TTATATGACA | AGACCAAGAG | GATATTCCTC | AAAGCAGAAA | GTGAAGAAGA |
| 1801 | AATTTTTGCG | CATCTGGGAT | TGGATTATAT | TGAACCGTGG | GAAAGAAATG | CCTAGGAAAG |
| 1861 | TGTTGTCAAC | ATTTTTTCCT | ATTCTTTTCA | AGTTAAATAA | ATTATGCTTC | ATATTAGTAA |
| 1921 | AAGATGCCAT | AGGAGAGTTT | GGGGTTATTT | AGGTCTTATT | GAAATGCAGA | TTGCTACTAG |
| 1981 | AAATAAATAA | CTTTGGAAAC | ATGGGAAGGT | GCCACTGGTA | ATGGGTAAGG | TTCTAATAGG |
| 2041 | CCATGTTTAT | GACTGTTGCA | TAGAATTC | | | | wherein A represents adenine, C represents cytosine, G represents guanine and T represents thymine.

* * * * *